US009180182B2

(12) United States Patent
van Kooyk et al.

(10) Patent No.: US 9,180,182 B2
(45) Date of Patent: Nov. 10, 2015

(54) METHOD FOR SUPPRESSING AN IMMUNE RESPONSE

(75) Inventors: Yvette van Kooyk, Amsterdam (NL); Wendy Unger, Amsterdam (NL)

(73) Assignee: VERENIGING VOOR CHRISTELIJK WETENSCHAPPELIJK ONDER WIJS, Amsterdam (NL)

( * ) Notice: Subject to any disclaimer, the term of this patent is extended or adjusted under 35 U.S.C. 154(b) by 0 days.

(21) Appl. No.: 13/994,599

(22) PCT Filed: Dec. 15, 2011

(86) PCT No.: PCT/EP2011/073006
§ 371 (c)(1),
(2), (4) Date: Nov. 18, 2013

(87) PCT Pub. No.: WO2012/080444
PCT Pub. Date: Jun. 21, 2012

(65) Prior Publication Data

US 2014/0072593 A1 Mar. 13, 2014

(30) Foreign Application Priority Data

Dec. 15, 2010 (EP) .................................... 10195279

(51) Int. Cl.
*A61K 39/385* (2006.01)
*A61K 39/00* (2006.01)

(52) U.S. Cl.
CPC ............... *A61K 39/385* (2013.01); *A61K 39/00* (2013.01); *A61K 39/0005* (2013.01); *A61K 39/0008* (2013.01)

(58) Field of Classification Search
CPC .............. A61K 39/00; A61K 39/0005; A61K 39/0008; A61K 39/385
See application file for complete search history.

(56) References Cited

U.S. PATENT DOCUMENTS

2001/0031266 A1 10/2001 Compans
2005/0201952 A1 9/2005 Sharma

FOREIGN PATENT DOCUMENTS

WO WO 2005/056047 A1 6/2005
WO WO 2011/073685 A1 6/2011
WO WO 2012/080444 A1 6/2012

OTHER PUBLICATIONS

Behan et al., The sad plight of multiple sclerosis research (low on fact, high on fiction): critical data to support it being a neurocristopathy, 2010, Inflammopharmacol 18:265-290.*

De Leon et al., Differential Influence of the Tumour-Specific Non-Human Sialic Acid Containing GM3 Ganglioside on CD4(+)CD25(−) effector and naturally occurring CD4(+)CD25(+) Regulatory T Cells Function, International Immunology, Apr. 2008, pp. 591-600, vol. 20, No. 4.

PCT International Search Report, PCT/EP2011/073006, dated Apr. 5, 2012.

PCT Written Opinion, PCT/EP2011/073006, dated Apr. 5, 2012.

PCT International Preliminary Report on Patentability, PCT/EP2011/073006 dated Jun. 18, 2013.

Dell et al., Glycoprotein Structure Determination by Mass Spectrometry, Science, Mar. 23, 2001, pp. 2351-2356, vol. 291.

Papini, Anna Maria, The use of post-translationally modified peptides for detection of biomarkers of immune-mediated diseases, Journal of Peptide Science, 2009, pp. 621-628, vol. 15.

European Patent Office Communication for copending application 11 799 680.1 dated Oct. 21, 2014.

European Search Report for copending application 11 799 680.1 dated Oct. 21, 2014.

Chinese Office Action for copending application 201180060393.X dated Aug. 5, 2014.

* cited by examiner

*Primary Examiner* — John Ulm
(74) *Attorney, Agent, or Firm* — TraskBritt, P.C.

(57) ABSTRACT

The invention is in the field of molecular immunology, more in particular in the field of medical treatment of animals such as humans suffering from unwanted immune reactions. The invention relates to methods for the treatment of unwanted immune reactions and provides means and methods for suppressing an immune response. The present invention relates in particular to regulatory T cells and methods of long-term, culture-expanding, activating and using same in immunotherapy and for the suppression of autoimmune responses, allergies and inflammatory diseases. The invention provides a sia alpha 2,3-conjugated antigen for use in the suppression of an immune response in a patient in need of such a treatment.

4 Claims, 20 Drawing Sheets

Figure 1A:
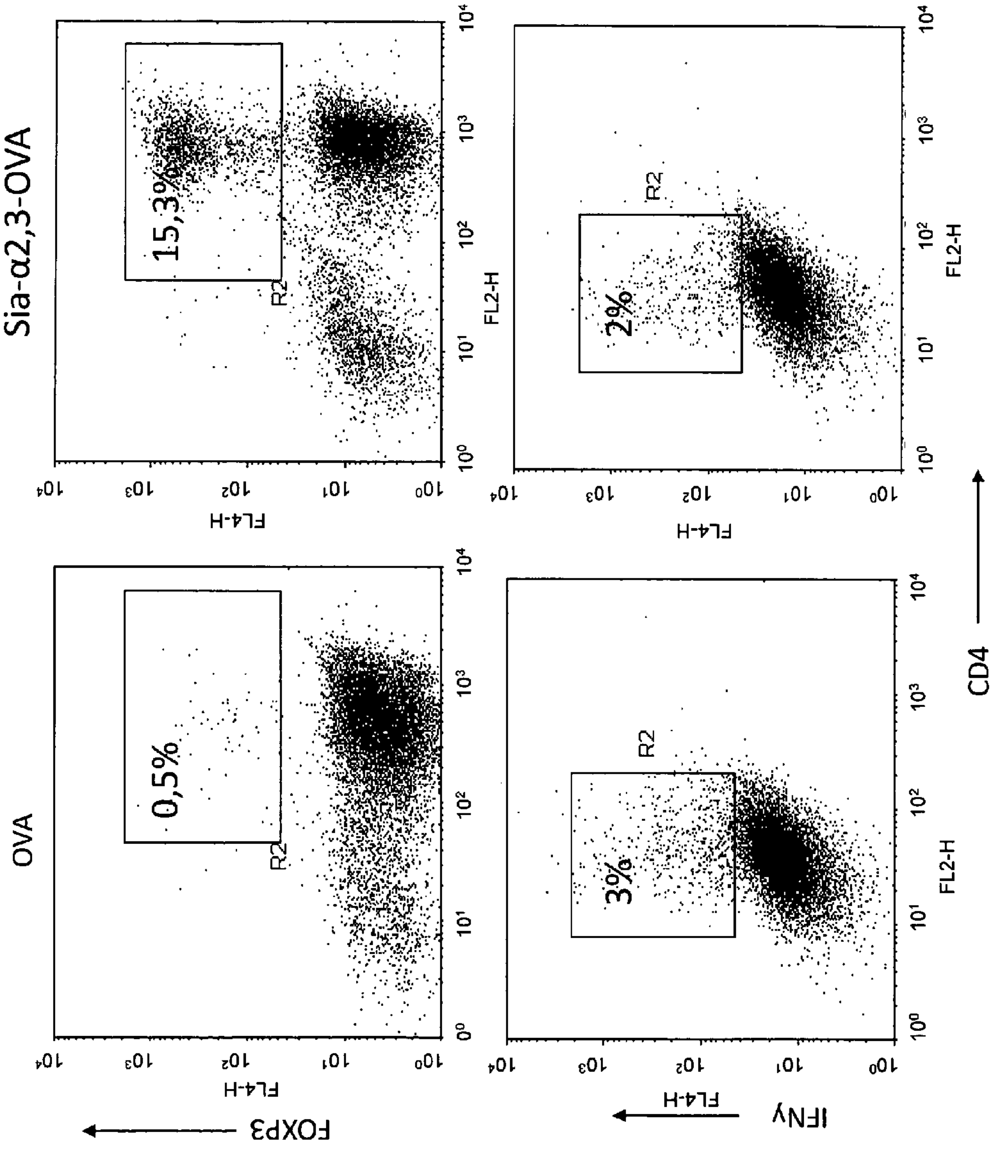

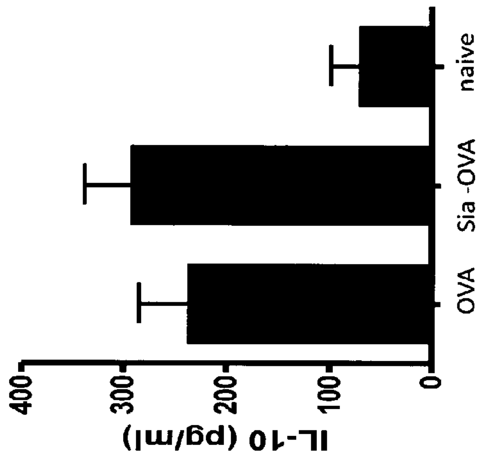
Fig. 7C
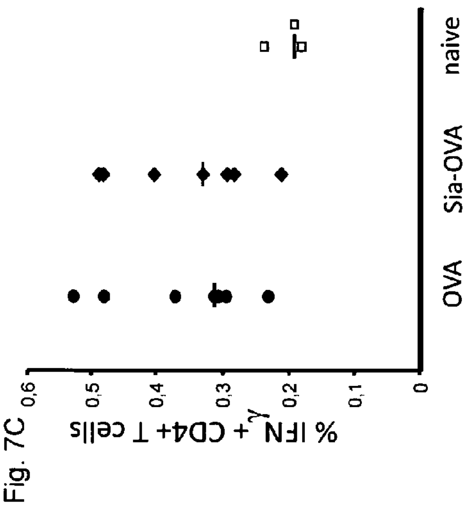
Fig. 7D
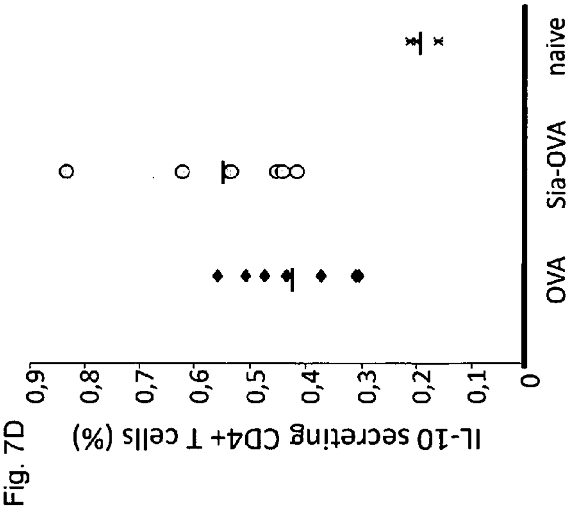

METHOD FOR SUPPRESSING AN IMMUNE RESPONSE

CROSS-REFERENCE TO RELATED APPLICATIONS

This application is a national phase entry under 35 U.S.C. §371 of International Patent Application PCT/EP2011/073006, filed Dec. 15, 2011, designating the United States of America and published in English as International Patent Publication WO 2012/080444 A1 on Jun. 21, 2012, which claims the benefit under Article 8 of the Patent Cooperation Treaty to European Patent Application Serial No. 10195279.4, filed Dec. 15, 2010.

FIELD OF THE INVENTION

The invention is in the field of molecular immunology, more in particular in the field of medical treatment of patients suffering from unwanted immune reactions. The invention relates to methods for the treatment of unwanted immune reactions and provides means and methods for suppressing an immune response. The present invention relates in particular to regulatory T cells and methods of long-term, culture-expanding, activating and using same in immunotherapy and for the suppression of autoimmune responses, allergies and inflammatory diseases.

BACKGROUND OF THE INVENTION

It has long been thought that suppressor cells play a role in the progression of cancer (Dye et al., J. Exp. Med. 154:1033-1042 (1981)). In fact, active suppression by T regulatory cells plays an important role in the down-regulation of T cell responses to foreign and self-antigens.

T cells are a class of lymphocytes, having specific T cell receptors (TCRs) that are produced as a result of gene rearrangement. T cells have diverse roles, which are accomplished by the differentiation of distinct subsets of T cells, recognizable by discrete patterns of gene expression. Several major T cell subsets are recognized based on receptor expression, such as TCR-[alpha]/[beta], and TCR [gamma]/[delta] and invariant natural killer cells. Other T cell subsets are defined by the surface molecules and cytokines secreted therefrom.

For example, T helper cells (CD4 cells) secrete cytokines, and help B cells and cytotoxic T cells to survive and carry out effector functions. Cytotoxic T cells (CTLs) are generally CD8 cells, and they are specialized to kill target cells, such as infected cells or tumor cells. Natural killer (NK) cells are related to T cells, but do not have TCRs, and have a shorter lifespan, although they do share some functions with T cells and are able to secrete cytokines and kill some kinds of target cells.

Human and mouse peripheral blood contains a small population of T cell lymphocytes that express the T regulatory phenotype ("Treg"), i.e., positive for both CD4 and CD25 antigens (i.e., those CD4-positive T cells that are also distinctly positive for CD25). First characterized in mice, where they constitute 6-10% of lymph node and splenic CD4-positive T cell populations, this population of CD4-positive CD25-positive cells represents approximately only 5-10% of human peripheral blood mononuclear cells (PBMC), or 2-7% of CD4-positive T cells, although some donors exhibit a more distinct population of CD4-positive and CD25-positive cells. About 1-2% of human peripheral blood PBMCs are both CD4 positive (CD4-positive) and CD25 brightly positive (CD25-positive) cells.

There are several subsets of Treg cells (Bluestone et al., Nature Rev. Immunol. 3:253 (2003)). One subset of regulatory cells develops in the thymus. Thymic derived Treg cells function by a cytokine-independent mechanism, which involves cell to cell contact (Shevach, Nature Rev. Immunol 2:389 (2002)). They are essential for the induction and maintenance of self-tolerance and for the prevention of autoimmunity (Shevach, Annu. Rev. Immunol. 18:423-449 (2000); Stephens et al., 2001; Turns et al., 2001; Thornton et al., 1998; Salomon et al., Immunity 12:431-440 (2000); Sakaguchi et al., Immunol. Rev. 182:18-32 (2001)).

These professional regulatory cells prevent the activation and proliferation of autoreactive T cells that have escaped thymic deletion or recognize extrathymic antigens, thus they are critical for homeostasis and immune regulation, as well as for protecting the host against the development of autoimmunity (Suri-Payer et al., J. Immunol. 157:1799-1805 (1996); Asano et al., J. Exp. Med. 184:387-396 (1996); Bonomo et al., J. Immunol. 154:6602-6611 (1995); Willerford et al., Immunity 3:521-530 (1995); Takahashi et al., Int. Immunol. 10:1969-1980 (1998); Salomon et al., Immunity 12:431-440 (2000); Read et al., J. Exp. Med. 192:295-302 (2000). Thus, immune regulatory CD4-positive CD25-positive T cells are often referred to as "professional suppressor cells."

However, Treg cells can also be generated by the activation of mature, peripheral CD4-positive T cells. Studies have indicated that peripherally derived Treg cells mediate their inhibitory activities by producing immunosuppressive cytokines, such as transforming growth factor-beta (TGF-[beta]) and IL-10 (Kingsley et al., J. Immunol. 168:1080 (2002); Nakamura et al., J. Exp. Med. 194:629-644 (2001)). After antigen-specific activation, these Treg cells can non-specifically suppress proliferation of either CD4-positive or CD25-positive T cells (demonstrated by FACS sorting in low dose immobilized anti-CD3 mAb-based co-culture suppressor assays by Baecher-Allan et al., J. Immunol. 167(3):1245-1253 (2001)).

Studies have shown that CD4-positive CD25-positive cells are able to inhibit anti-CD3 stimulation of T cells when co-cultured with autologous antigen presenting cells (APC), but only through direct contact (Stephens et al., Eur. J. Immunol. 31:1247-1254 (2001); Taams et al., Eur. J. Immunol. 31:1122-1131 (2001); Thornton et al., J. Exp. Med. 188:287-296 (1998)). However, in mice this inhibitory effect was not able to overcome direct T cell stimulation with immobilized anti-CD3 or with anti-CD3/CD28 (Thornton et al., 1998). In previous reports, human CD4-positive CD25-positive T cells isolated from peripheral blood required pre-activation in order to reveal their suppressive properties, as direct culture of the regulatory cells was generally insufficient to mediate suppressive effects (Dieckmann et al., J. Exp. Med. 193: 1303-1310 (2001)).

Others have also found that the inhibitory properties of human CD4-positive CD25-positive T cells are activation-dependent, but antigen-nonspecific (Jonuleit et al., J. Exp. Med. 193:1285-1294 (2001); Levings et al., J. Exp. Med. 193(11):1295-1302 (2001); Yamagiwa et al., J. Immunol. 166:7282-7289 (2001)), and have demonstrated constitutive expression of intracellular stores of cytotoxic T lymphocyte antigen-4 (CTLA-4) (Jonuleit et al., 2001; Read et al., J. Exp. Med. 192:295-302 (2000); Yamagiwa et al., 2001; Takahashi et al., J. Exp. Med. 192:303-310 (2000)). Moreover, after T-cell receptor (TCR)-mediated stimulation, CD4-positive CD25-positive T cells suppress the activation of naive CD4- positive CD25-negative T cells activated by alloantigens and mitogens (Jonuleit et al., 2001).

Both mouse and human Treg cells express CTLA-4, however the role of CTLA-4 in tolerance induction and its capacity to impart inhibitory function to regulatory CD4-positive CD25-positive T cells is controversial. CTLA-4 (also known as CD152) is a homolog of CD28 and is a receptor for the CD80 and CD86 ligands. CTLA-4 inhibits T cell responses in an antigen and TCR-dependent manner. T cells that have impaired CTLA-4 function have enhanced T cell proliferation and cytokine production. In contrast, enhanced CTLA-4 function leads to inhibited cytokine secretion and impaired cell cycle progression both in vitro and in vivo. In the mouse, CTLA-4 is not required for suppressive function of the Treg cells, as opposed to its requirement in humans.

A recent study has shown that Treg cells grow extensively in vivo (Tang, J. Immunol. 171:3348 (2003)), while others have suggested that the efficacy of therapeutic cancer vaccination in mice can be enhanced by removing CD4-positive CD25-positive T cells (Sutmuller et al., J. Exp. Med. 194: 823-832 (2001)). Studies have also indicated that depletion of regulatory cells led to increased tumor-specific immune responses and eradication of tumors in otherwise non-responding animals (Onizuka et al., Cancer Res. 59:3128-3133 (1999); Shimizu et al., J. Immunol. 163:5211-5218 (1999)). Susceptible mouse strains that were made CD4-positive CD25-positive deficient by neonatal thymectomy were shown to develop a wide spectrum of organ-specific autoimmunities that could be prevented by an infusion of CD4-positive CD25-positive T cells by 10-14 days of age (Suri-Payer et al., J. Immunol. 160:1212-1218 (1998)). That study also found that CD4-positive CD25-positive T cells could inhibit autoimmunity induced by autoantigen-specific T cell clones. The transfer of CD4-positive CD25-negative T cells into nude mice also reportedly led to the development of autoimmune disorders which could be prevented by the co-transfer of CD4-positive CD25-positive T cells using lymphocytes first depleted of CD25-positive cells (Sakaguchi et al., J. Immunol. 155:1151-1164 (1995)).

Hereafter, the transcription factor Forkhead box P3 (FoxP3) was related to the generation and fuction of naturally occurring Treg. Mice in which FoxP3 protein was deleted due to a mutation in the FoxP3 gene, developed severe autoimmune syndroms and wasting diseases (socalled "scurfy" mice; Brunkow et al., Nat Genet. 27:68-73, 2001). This seminal discovery enabled to attribute the cause of the X-linked IPEX syndrome (Immunodysregulation, Polyendocrinopathy, and Enteropathy, X-linked) in humans to a mutation in the FoxP3 gene (Bennett et al. Nat Genet. 27: 20-21; 2001). Later studies also demonstrated the presence of FoxP3 in some adaptive Treg subsets.

However, data also indicate that the role of CD4-positive CD25-positive cells is not limited to self-tolerance and the prevention of autoimmunity. While few studies have addressed the role of CD4-positive CD25-positive T cells in alloresponses or in transplantation, CD4-positive CD25-positive T cells have been reported to prevent allograft rejection, both in vitro and in vivo (Hara et al., J. Immunol. 166: 3789-3796 (2001); Taylor et al., J. Exp. Med. 193:1311-1318 (2001)). Allogeneic stimulation of human T cell proliferation is also blocked by CD4-positive CD25-positive T cells (Yamagiwa et al., 2001), whereas Wood's laboratory has shown that CD4-positive CD25-positive T cells suppress mixed lymphocyte responses (MLR), but only when the alloantigen was presented by the indirect, and not the direct, pathway of allorecognition (Hara et al., 2001). It is likely that direct antigen presentation occurs between the regulatory T cells and the anti-CD3/28 stimulated responder T cells, as the sorted CD4-positive 25-positive cells are highly depleted of professional APC.

The absence of Tregs or depletion of Tregs is shown to result in the development of auto-immunity, such as Type 1 Diabetes, Inflammatory bowel disease (IBD), thyroididites, Multiple Sclerosis and Systemic lupus erythematosus (SLE). Moreover the disease can be reversed by the adoptive transfer of CD4+CD25+Treg cells. Besides a deficiency in Treg number, T cell regulation in autoimmunity has also been shown to fail due to a deficiency in the function of Treg to inhibit effector T cells. It is clear that defects in Treg cell number and function can contribute to disease and therapies directed at these defects have the potential to prevent and also cure these diseases. Animal studies suggest that an increase in Treg cell number at the site of inflammation is likely to be therapeutic in autoimmunity. This can be achieved by adoptive transfer of in-vitro expanded autologous Tregs or by the use of agents that promote Treg cell proliferation, survival and induction. The identity of factors that influence cell number and function of Tregs are not clearly identified at the moment, and may be crucial for the application of autoimmune diseases.

Antigen Presenting cells such as DC are known for their capacity to differentiate naive CD4 T cells into different lineage of T cells, such as Th1, Th2, Th17 and Treg. Recent studies demonstrate that a population of gut DC, particularly lamina propria CD103+ DCs, can promote the conversion of naive CD4+ T cells into FoxP3+ iTregs through the secretion of retinoic acid (RA) in conjunction with TGF-β. DC express various receptors such as CD80/86 that can be bound by CTLA-4 on Tregs that triggers the induction of the enzyme indoleamine 2,3 dioxygenase (IDO) in DC. IDO converts tryptophan into pro-apoptotic metabolites that suppress effector T cells. On the other hand engagement of MHC class II on DC by LAG3 on Tregs suppresses APC maturation and reduces their ability to activate T cells. These findings demonstrate that DC may differentiate CD4 T cells into Tregs. However, little is still known on the mechanism and signals that reach DC to instruct CD4 naïve T cells to differentiate into Tregs.

Patients suffering from autoimmune diseases or inflammatory diseases would greatly benefit from treatments wherein the Treg numbers or function are improved.

Applicants have established that the uptake of specific glycosylated antigens by DCs regulates the number and function of Tregs. This opens new opportunities for the treatment of unwanted immune reactions and leads to new methods and means for the treatment of autoimmune diseases and inflammatory diseases.

SUMMARY OF THE INVENTION

We found that sialic acids on self and non-self antigens play an important role in the induction of tolerance. As a model system, applicants investigated the well-known food allergy against ovalbumin (OVA). Ovalbumin is the major allergen in chicken egg. In humans, CD4 T-cell responses against OVA have been detected (Heine et al, Currebt Allergy and Asthma reports 6, 145-152, 2006). To study responses in mice, T-cell receptor transgenic mice have been generated that express a OVA-specific TCR on all CD4 T-cells (OT-II transgenic mice). These mice are widely used.)

We therefore set out to modify the model antigen OVA with Neu5Acα2-3Galβ1-4Glc, creating sia-alpha 2,3-OVA and assessed the functional consequences on $CD4^+$ T-cell activation and differentiation upon co-culture with sia-2,3-OVA-loaded DC.

It was established that such a sia alpha 2,3-conjugated antigen was capable of suppressing an immune response and could therefore advantageously be used in the suppression of an immune response in a patient allergic to ovalbumin.

In a more general concept, the invention therefore relates to a sia alpha 2,3-conjugated antigen for use in the suppression of an immune response in a patient in need of such a treatment.

DETAILED DESCRIPTION OF THE INVENTION

Sialic acids are the most prevalent terminal monosaccharide on the surface of mammalian cells. The most common mammalia sialic acids are N-acetylneuraminic acid (Neu5Ac) and N-glycolyneuraminic acid (Neu5Gc). Humans are unable to synthesize Neu5Gc due to an irreversible mutation in the gene encoding the enzyme responsible for conversion of Neu5Gc from Neu5Ac. Sialic acids may be α2,3-, α2,6- or α2,8-linked to the underlying glycan. Sialic acids are often found at the outer ends of surface exposed oligosaccharide chains, attached to proteins and lipids. In this terminal position, they serve as ligands for lectins such as Sialic acid binding Ig-like lectins (Siglecs).

We started by assessing whether conjugation of alpha-sia-2,3 to OVA (hereafter referred to as OVA-sia-2,3) essentially affected OVA-specific CD4+ T-cell responses in-vitro. Hereto, naive CD4+CD62Lhi CD25− T-cells were isolated from OT-II mice and co-cultured with BMDC that had been loaded with OVA-sia-2,3 or native OVA for 4 h. Six days later, CD4 T helper differentiation was analysed by staining for FoxP3 or intracellular IFNγ. We observed that naive CD4+ T-cells were converted into FoxP3+ T-cells when primed by DC loaded with OVA-sia-2,3 (FIG. 1A, upper panels).

Figure 1B:
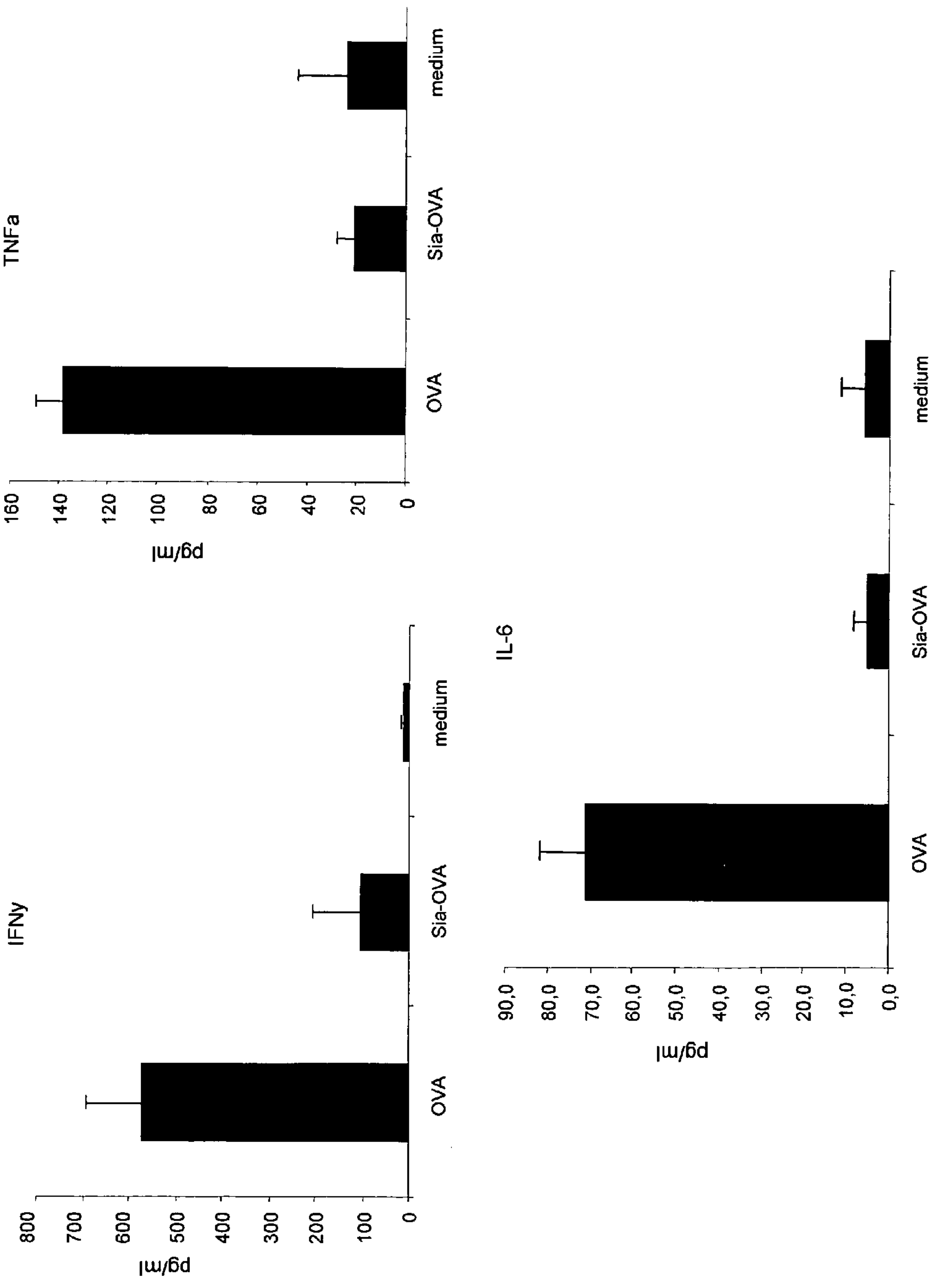
Figure 1B:
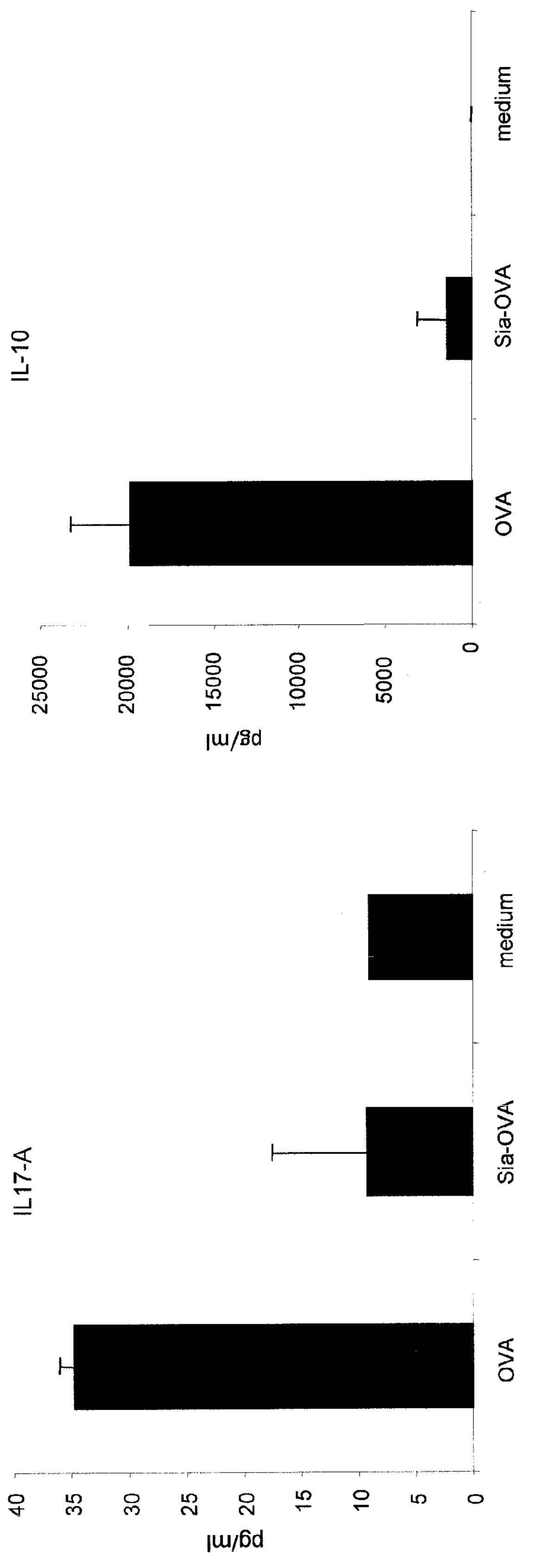

DC loaded with native OVA did not prime T-cells to differentiate into Treg. By contrast, these T-cells were converted into effector T-cells as shown by IFNγ staining (FIG. 1A, lower panels). This was confirmed when examining the supernatant of these cultures (FIG. 1B, upper panel). In addition high levels of the T-cell effector cytokines TNFα and IL-6 were detected in these cultures. By contrast, these were virtually absent in cultures of T-cells primed by OVA-sia-2,3 DC. Since the generation of FoxP3+ Treg is closely related to Th17 generation, we assessed the presence of Th17 cells by analysing IL17A in the supernatant. No significant amounts of IL17A were detectable in the supernatant of OVA-sia2,3 DC-T-cell co-cultures.

Moreover, we observed that the amount of Th1 effector cytokines IFNγ and TNFα was still significantly lower when naïve T-cells were primed by OVA-sia-2,3-DC than by OVA-DC in the presence of Th1- or Th17-promoting stimuli (FIG. 1C). Only in the presence of the Th17-promoting agent prostaglandin (PGN) high levels of IL17A were detected in cultures with OVA-sia-2,3-DC. No significant amounts of IL10 were detected in the DC-T-cell co-cultures (data not shown).

Together, these data show that priming of naive CD4 T-cells by OVA-sia2,3 loaded DC promotes de novo generation of FoxP3+ T-cells. Furthermore, the generation of effector T-cells is prevented, even in a Th1- or Th17-promoting environment. However, more IL17A secreting T-cells are present when naïve CD4+ T-cells are primed by OVA-sia-2,3 loaded DC in a Th17-skewing milieu.

Figure 2A:
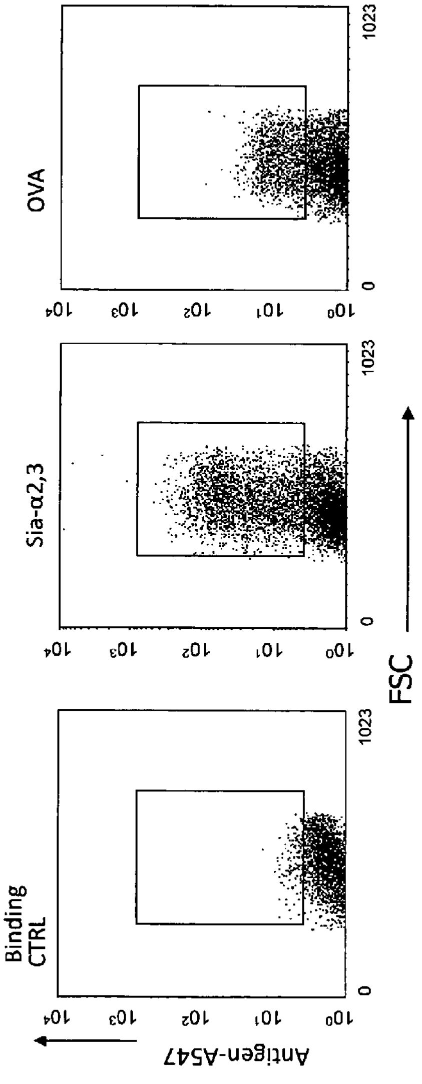

As a control, the following experiment was performed. The generation of FoxP3+ T cells in the absence of effector T-cells upon priming of naive CD4 T-cells with OVA-sia-2,3 loaded DC could theoretically be the result of low amounts of antigen presented by the DC in MHC class II molecules. To address this, we incubated BM DC with fluorescent labeled OVA-sia-2,3 and assessed both binding as well as uptake at various time points. It is clear from FIGS. 2A and B that modification of OVA with sia-2,3 results in significant better binding and uptake by BMDC compared to nonmodified OVA. Thus, the uptake of OVA-sia-2,3 by BMDC is increased.

Despite this increased uptake, it is possible that OVA-sia-2,3 is rapidly degraded upon internalization. To rule out this possibility, we subsequently used these antigen-loaded DC in an antigen-presentation assay with purified OVA-specific CD4+ T-cells. Native OVA is well presented in MHC class II molecules as shown by significant T-cell proliferation (FIG. 2C). The proliferation of the CD4+ T-cells was only significantly different when a high dose of sialic acid-conjugated OVA was used. At lower doses no significant difference in CD4 T-cell proliferation induced by DC loaded with native OVA or sia-2,3-OVA was detected. These data may indicate that OVA-sia-2,3 enters a similar processing and presentation pathway as native OVA.

Figure 3A:
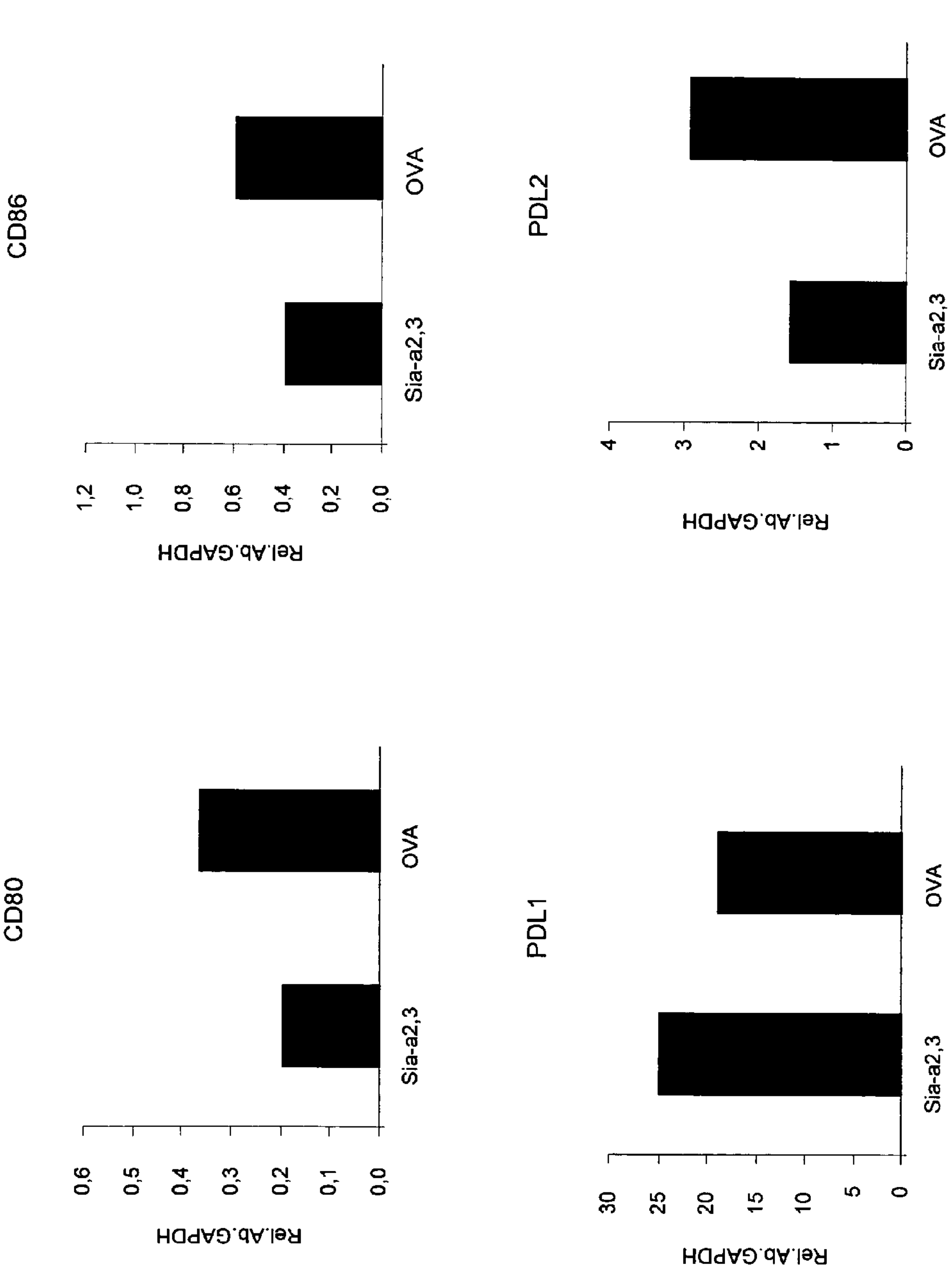

In view of the data on antigen uptake and presentation, we hypothesized that uptake of OVA-sia-2,3 triggers a signaling cascade, resulting in modulation of the DC phenotype. Therefore we examined the expression of costimulatory molecule transcripts in BMDC upon 6h incubation with OVA-sia-2,3 and compared it with expression in BMDC incubated with native OVA or BMDC incubated in medium only. From FIG. 3A it is clear that the expression of CD80 and CD86 is lower on BMDC incubated with OVA-sia-2,3 than with native OVA, albeit not significantly. Similar data were obtained for CD40 and MHC-class II (data not shown). Furthermore, molecules associated with tolerance were not distinctively or higher expressed by the OVA-sia-2,3-loaded BMDC. Moreover, the expression of PD-L2 seems to be decreased on OVA-sia-2,3-loaded BMDC.

Figure 3B:
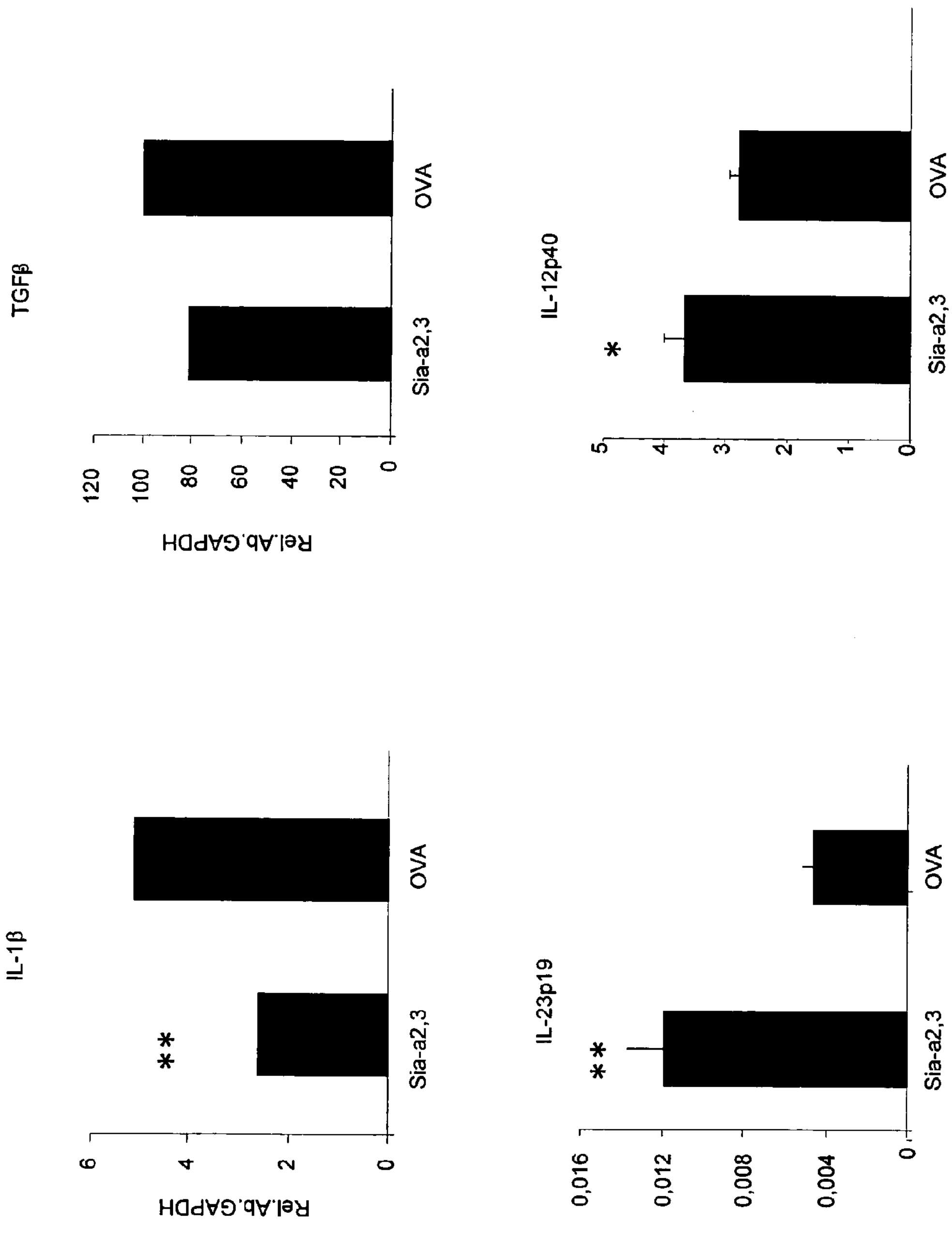

Analysis of cytokine mRNA expression revealed a significant lower expression of IL1β levels in OVA-sia-2,3-loaded DC (FIG. 3B). By contrast, the expression of IL23p19, which can associate with the p40 subunit of IL12 to form IL23, was significantly elevated in OVA-sia-2,3-loaded DC. Furthermore examination of mRNA encoding the anti-inflammatory cytokines IL10 or TGFb revealed no significant difference (FIG. 3B).

Together, these data indicate that uptake of OVA-sia-2,3 in the absence of additional stimuli does not result in expression of well known tolerogenic markers. We have therefore demonstrated that a sia-2,3 modified antigen taken up by DC modifies the differentiation of naive CD4 T cells into Tregs. Our data demonstrate that this is not the result of low dose of antigen presentation, as high antigen dose were taken up, similar as un-modified antigen or sia-2,6 modified antigens. We have analysed whether the uptake of sia-2,3 may modify the tolerogenic phenotype of DC, but we did not see any major alterations in the expression of CD80/CD86, CD40 or MHC class II. We observed that the expression of the co-stimulatory molecule PDL-2 was lower on DC that had taken up OVA-sia-2,3 compared to native OVA. Upon analysis of the cytokine production by DC we observed that the inflammatory cytokine profile IFNy, IL-6 and TNFa) was reduced by DC upon uptake of OVA-sia-2,3, illustrating a potentiation towards an anti-inflammatory signature. When analysing the anti-inflammatory cytokine profile we observed little enhanced production of TGFb and no alterations in IL-10 and IL17A.

Our finding that alpha-2,3 sialylation of antigen enhances the differentiation of antigen specific FoxP3+ regulatory T cells, sheds new light on how on the mechanism and signals that reach DC to instruct CD4 naive T cells to differentiate into Tregs. It also enables a whole new area of treatment for autoimmune diseases and inflammatory diseases. The invention therefore relates to a sia alpha 2,3-conjugated antigen for use in the suppression of an immune response in a patient in need of such a treatment.

The term sia-alpha 2,3 conjugated antigen refers to an antigen such as a protein, polypeptide, lipid or otherwise, covalently attached to the sialic acid Neu5Acα2-3Galβ1-4Glc, creating sia-alpha 2,3-conjugated antigen.

Such an antigen may effectively be used for the treatment of autoimmune diseases such as multiple sclerosis, rheumatoid arthritis, diabetes type 1, gastritis and inflammatory bowel disease. It may also be used for the treatment of inflammatory diseases, such as psoriasis, allergy, Alzheimer's disease, Parkinson's disease and transplantation.

In another embodiment, the invention relates to a method for suppressing an immune response in a patient in need of such a treatment wherein a sial alpha 2,3 modified antigen is administered to said patient.

It may be envisaged that the immune response is even better suppressed when disease-specific antigens are sialylated and administered to patients. The invention therefore also relates to a sia alpha 2,3-conjugated antigen for use in the suppression of an immune response in a patient in need of such a treatment wherein the antigen is disease-specific. Several examples of disease specific antigens that work well in the methods according to the invention are listed in table 1.

TABLE 1

| Disease | Disease-specific antigens |
|---|---|
| Multiple Sclerosis | Myelin, MOG |
| Rheumatoid Arthritis | citrullinated proteins; human cartilage gp39; HSP70, HSP60; type II collagen |
| Type 1 Diabetes | preproinsulin; GAD65; IGRP; IA-2; preproIAPP; Zinctransporter 8 |
| Allergies | Animal products Fel d 1 (cat allergy) fur and dander; cockroach calyx; wool; dust mite excretion. penicillin; sulfonamides; salicylates local anaesthetics, celery and celeriac; corn or maize; eggs, fruit; pumpkin, beans; peas; peanuts; soybeans; milk; seafood; sesame; soy; tree nuts; pecans; almonds; wheat. bee sting venom; wasp sting venom; mosquito stings, latex, metal, Plant pollens (hay fever) grass, ryegrass, timothy-grass weeds, ragweed, plantago, nettle, artemisia vulgaris, chenopodium album, sorrel trees, birch, alder, hazel, hornbeam, aesculus, willow, poplar, platanus, tilia, olea, Ashe juniper. |

In this way one would modify specific antigens, related to the disease, as proteins, or peptides, or as nanoparticules or encapsulated particules, and use the alpha 2,3 sialic acid as the glycan structure that can ex-vivo or in-vivo instruct APC such as DC to start an anti-inflammatory program and enhance the induction of Tregs that dampen the inflammations and will recover the disease.

LEGEND TO THE FIGURES

Figure 1:
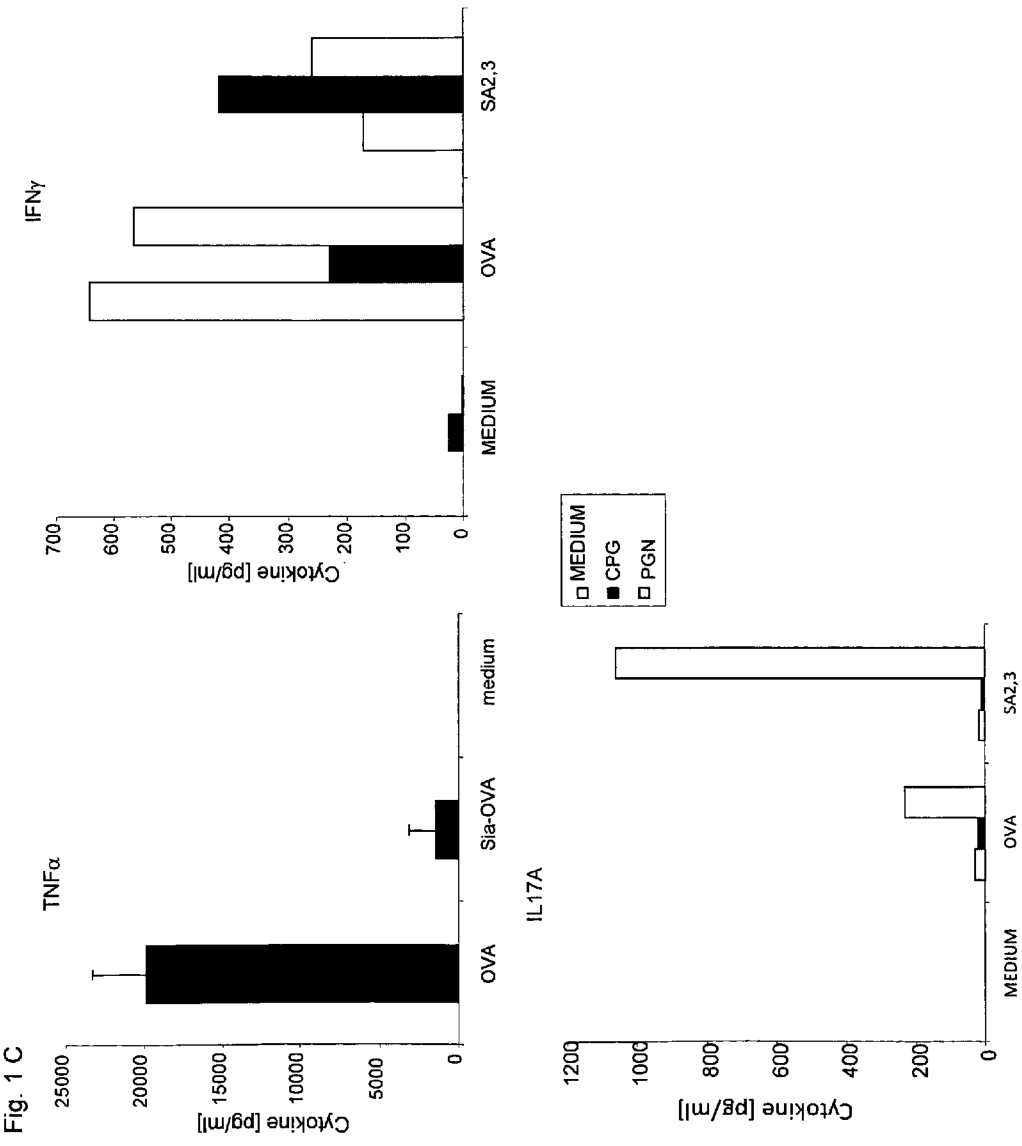

FIG. 1: Priming of naive CD4 T-cells with OVA-sia-2,3-loaded DC results in de novo generation of FoxP3+ T-cells and prevents effector T-cell formation.

A. Immature BMDC were incubated with 50 ug/ml OVA or OVA-sia-2,3 for 4 hours. After extensive washing, naive OVA-specific CD4 T-cells were added at a 1:10 ratio. On day 6 of culture, cells were harvested, fixed and permeabilised and stained for CD4 and FoxP3 (upper panel) or, after 6 h stimulation with PMA/ionomycin/BrefeldinA, for IFNγ (lower panel). Results are representative of five independent experiments. B, supernatants of these cultures were examined for the presence of effector T-cell cytokines (IFNγ, TNFα, 1L6, and Il17A) as well as the anti-inflammatory cytokine IL10. C. The amount of effector T-cell cytokines IFNγ and TNFα is also reduced when CpG or PGN were added to co-cultures containing OVA-sia-2,3-loaded DC. Only in the presence PGN, OVA-sia-2,3-loaded DC promote Th17 differentiation. Depicted results are representative of four independent experiments.

Figure 2B:
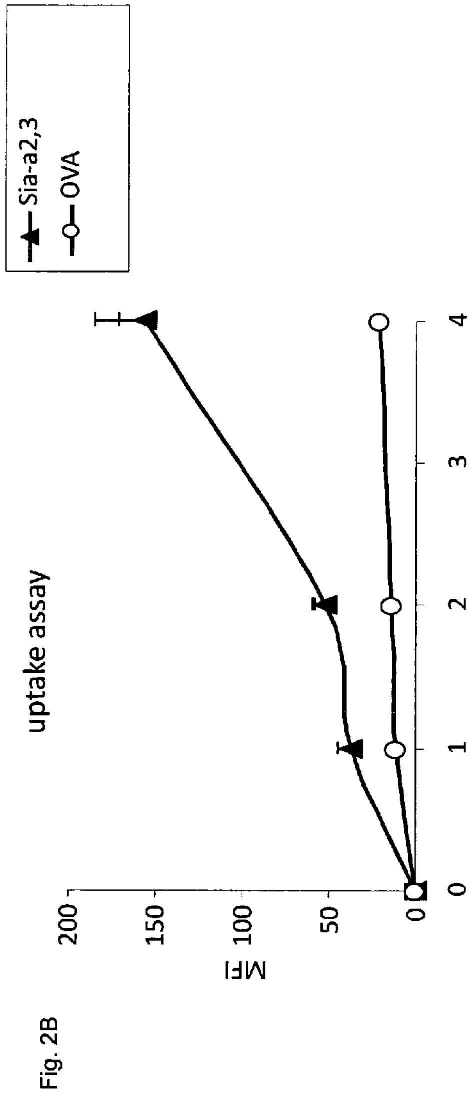
Figure 2C:
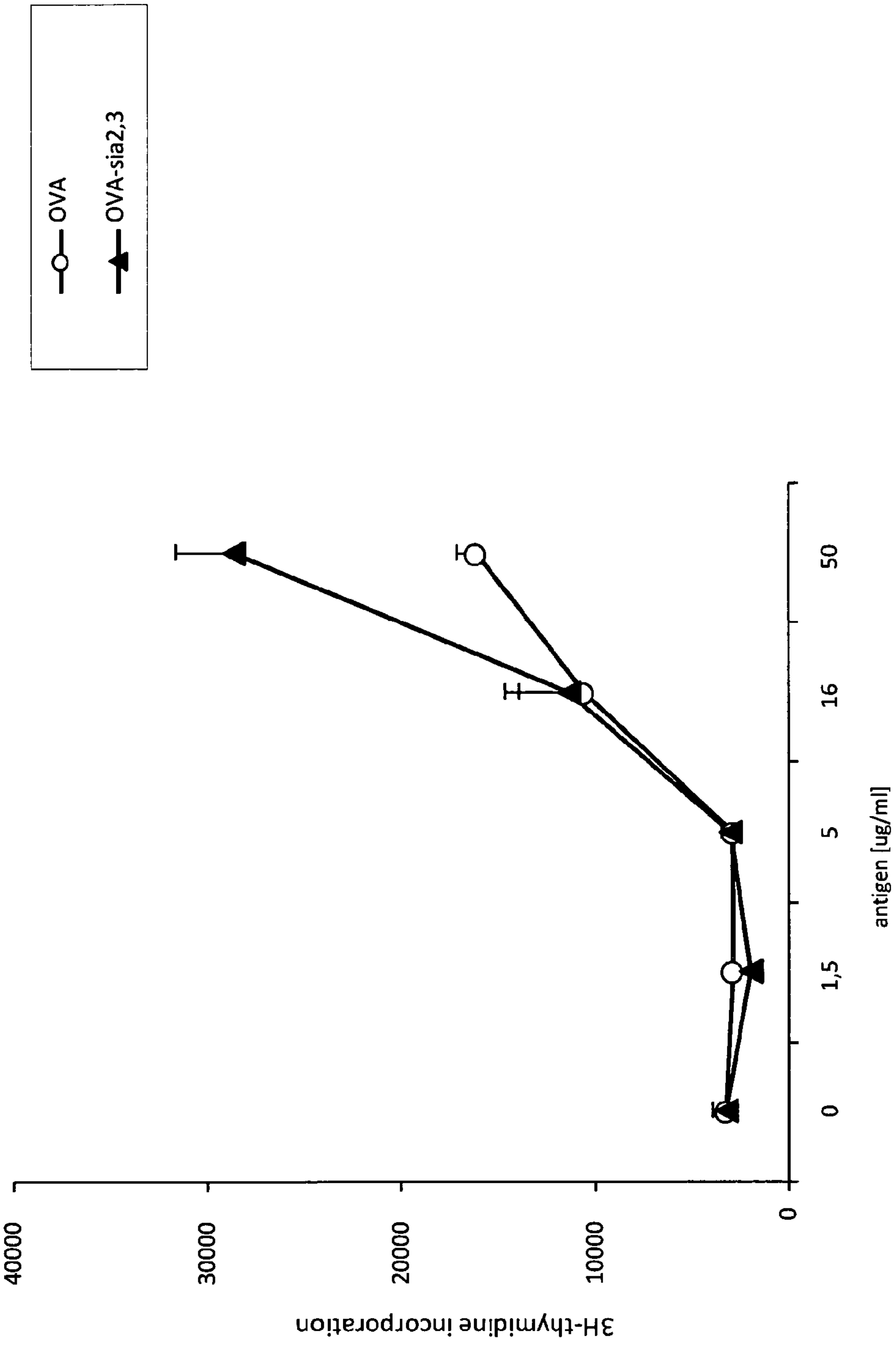

FIG. 2: No enhanced MHC class II presentation of OVA-sia-2,3 despite increased binding and uptake by DC.

The OVA-neo-glycoconjugate OVA-sia-2,3 was fluorescently labeled to assess binding and uptake by BMDC. A, To assess binding of the neo-glycoprotein, $10^5$ BMDC were incubated with 50 μg/ml of antigen for 30 min at 4 C. Binding was compared with native OVA. CTRL indicates cells incubated with medium only, which were used to as negative control. Binding was assesed by flow cytometry. Representative facs plots are shown. B, In addition, uptake was determined by incubating BMDC with 50 μg/ml of antigen at 37 C. Uptake of antigen was determined at indicated time points using flow cytometry and represented as MFI. One representative experiment out of three is shown. C. To examine whether increased uptake of OVA-sia-2,3 also increased presentation in MHC class II, we co-cultured $2.5\times10^4$ CD11c$^+$ BMDC, pulsed with indicated concentrations of OVA-sia-2,3 or native OVA, with purified OVA-specific CD4$^+$ T-cells. Proliferation was determined by addition of 3H-Thymidine during the last 16 h of a three day culture period.

FIG. 3: No induction of a tolerogenic signature in BMDC after incubation with OVA-sia-2,3.

To examine whether incubation of BMDC with OVA-sia-2,3 induced a tolerogenic phenotype in BMDC, we incubated $10^5$ BMDC with 50 μg/ml of antigen. This was compared with the phenotype induced by incubation of BMDC with native OVA. Six hours later, RNA was isolated and expression of A. co-stimulatory markers and B. cytokines was examined using RT-PCR. One representative experiment out of three is shown. P-value $<0.05$ was considered significantly different from responses to native OVA.

Figures 4A, 4B:
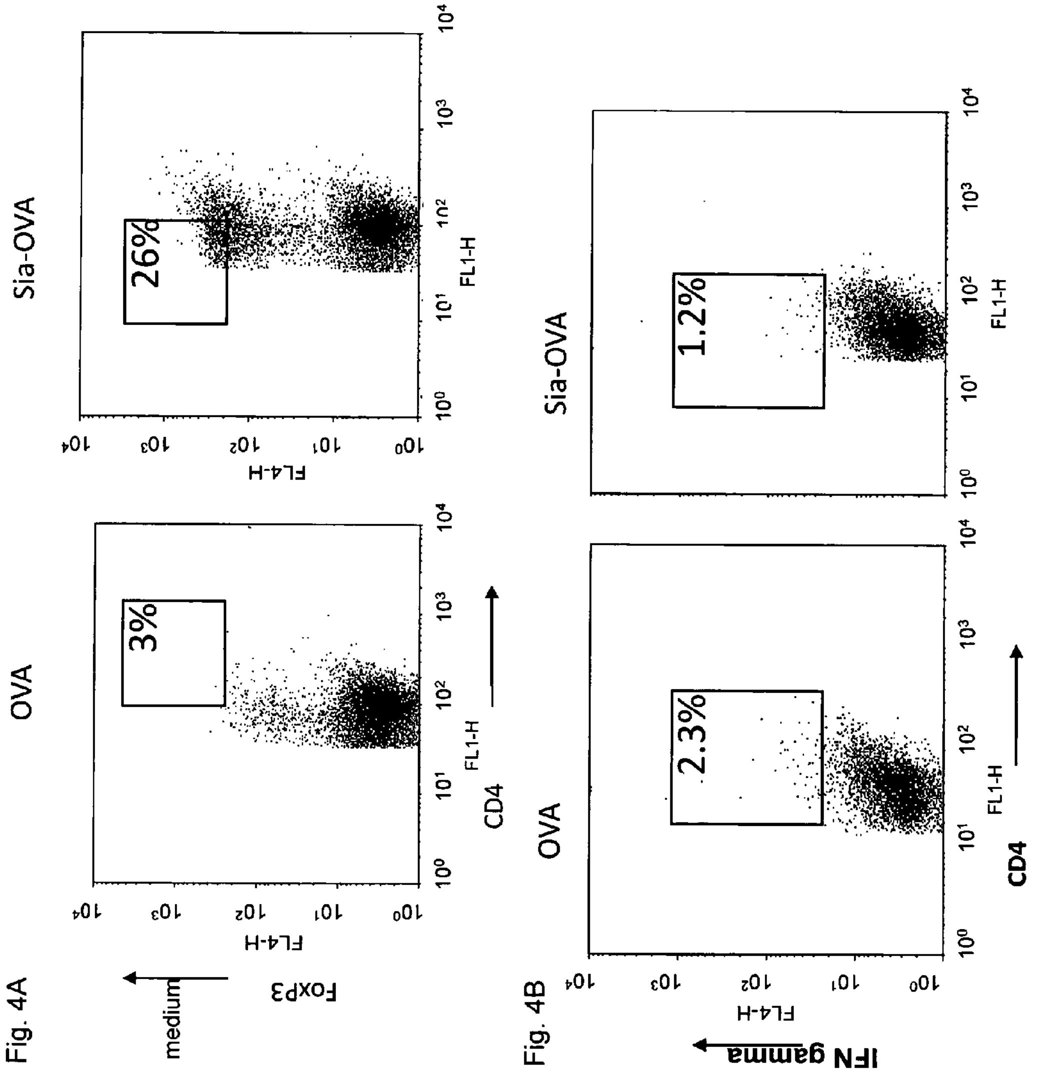
Figure 4C:
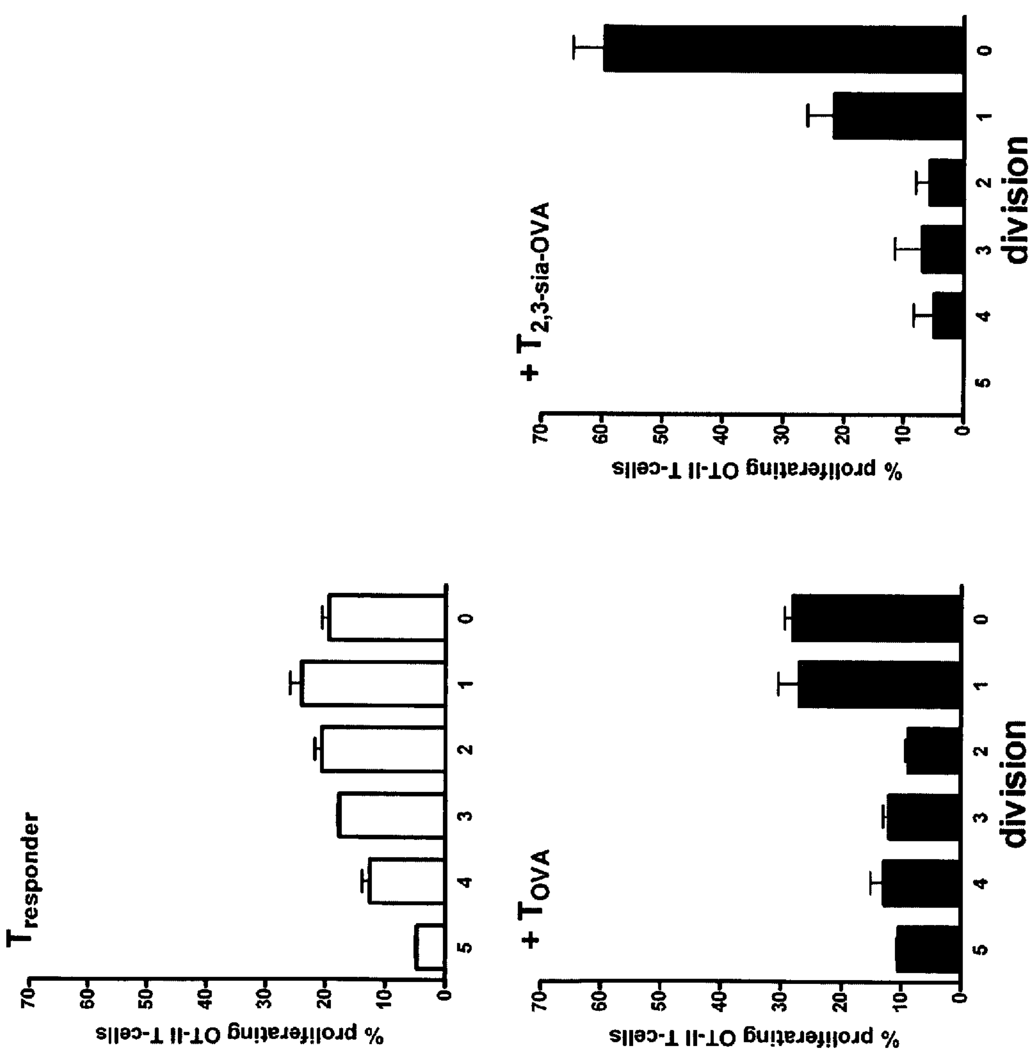
Figure 4D:
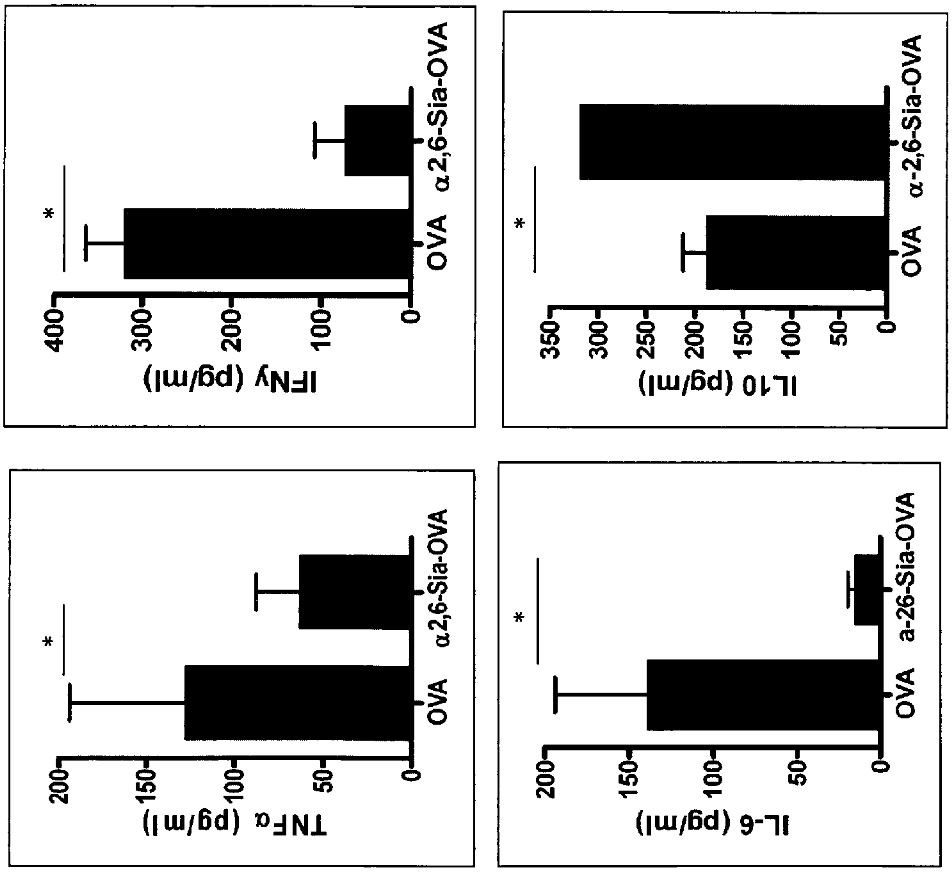

FIG. 4: Priming of naive CD4 T-cells with Sia-OVA-loaded ex-vivo isolated splenic DC results in de novo generation of FoxP3+ T-cells with suppressive properties.

Ex-vivo isolated CD11c$^+$ splenic DC were incubated with 50 ug/ml Sia-OVA or native OVA for 4 hours. After extensive washing, naïve OVA-specific CD62L$^{hi}$CD4$^+$ T-cells were added at a 1:10 ratio. On day 6 of culture, cells were harvested, fixed and permeabilised and stained for CD4 and FoxP3 (A) or, after 6 h stimulation with PMA/ionomycin/BrefeldinA, for IFNγ (B). The supernatants of the cultures were examined for the presence of effector cytokines (IFNγ, TNFα, IL6) as well as the anti-inflammatory cytokine IL10 (D). In addition, by adding these T-cells to co-cultures of naive CFSE-labeled OT-II T-cells and OVA-loaded DC at a 1:1 ratio, potential suppressive properties could be evaluated. The proliferation of responder T-cells was analysed 4 days later using flow cytometry (C). Results are representative of two independent experiments.

FIG. 5: Uptake of sialylated antigen results in tolerogenic DC even in the presence of a pro-inflammatory stimultus.

Ex-vivo isolated splenic DC were incubated with 50 ug/ml Sia-OVA in the presence of 100 ng/ml LPS. Four hours later, cells were extensively washed and naïve OVA-specific CD62L$^{hi}$ CD4$^+$ T-cells were added at a 1:10 ratio. On day 6 of culture, cells were harvested, fixed and permeabilised and stained for CD4 and FoxP3 (A, upper panel) or, after 6 h stimulation with PMA/ionomycin/BrefeldinA, for the effector cytokine IFNγ (A, lower panel). In addition, the culture supernatants were analysed for the presence of effector cytokines (IFNγ, TNFα, IL6) (B).

FIG. 6: De novo induction of $FoxP3^+$ T cells upon intravenous injection of Sia-OVA.

Figure 6A:
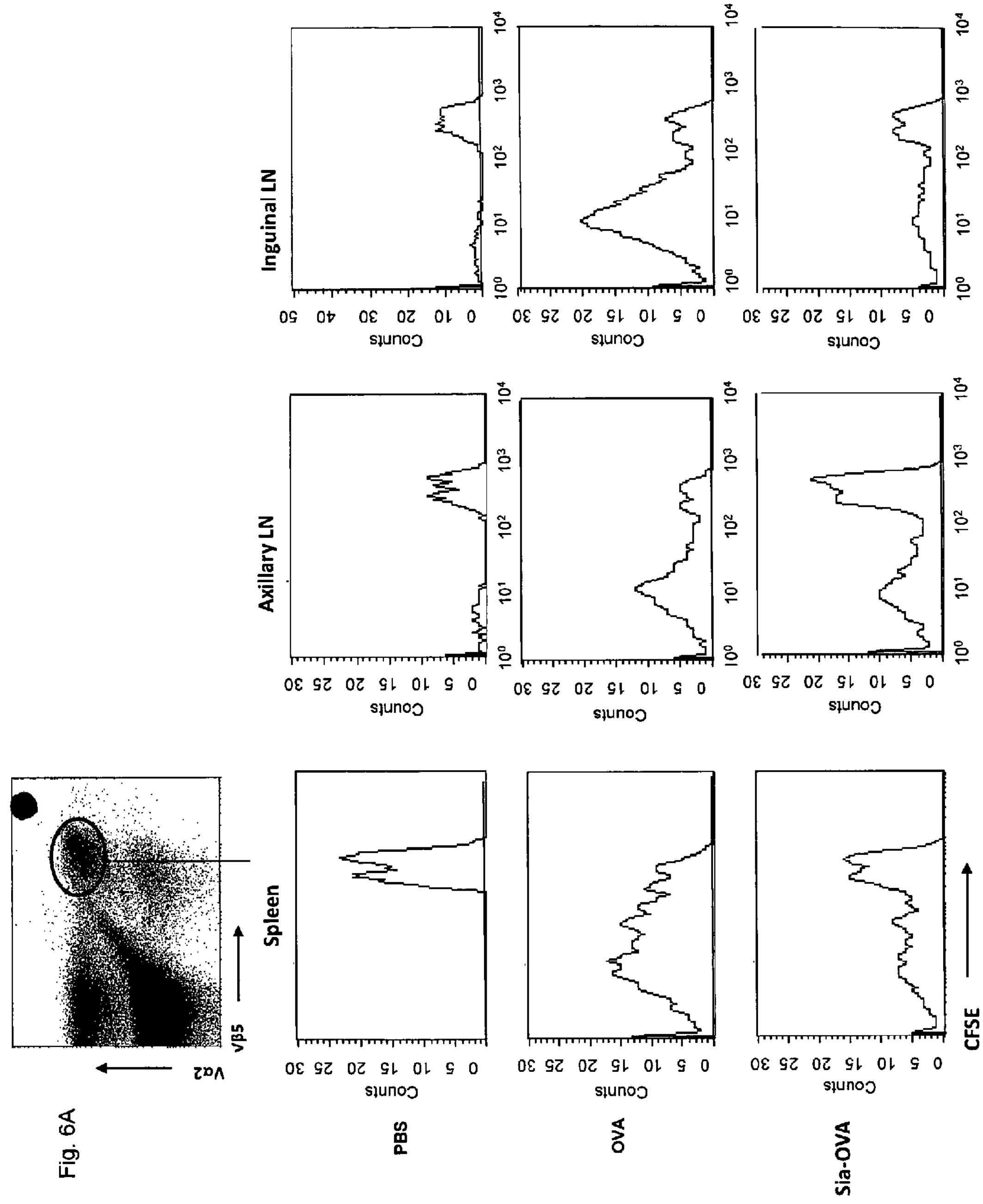

FIG. 6A: C57BL/6 mice transferred with CFSE-labeled OT-II T-cells and one day later injected with PBS; OVA or Sia-OVA intravenously. Analysis of OT-II T cells (identified based on Tg T-cell receptor) for dilution of CFSE in spleen (left) and lymph nodes (right) FIG. 6B: C57BL/6 mice transferred with CFSE-labeled OT-II T-cells one day later injected with PBS; OVA or Sia-OVA subcutaneously Analysis of spleens (left) and lymph nodes (right). To examine whether Sia-OVA also has tolerogenic properties in-vivo we injected C57BL/6 mice that were adoptively transferred with CFSE labeled $CD4^+$ $CD25^-$ OT-II cells with 100 ug Sia-OVA i.v. (A) or s.c. (B). This was compared with injection of 100 ug OVA. Control mice received PBS. Four days later, the spleen and axillary and inguinal lymph nodes were isolated and single cell suspensions were stained for Tg TCR (Valfa2, Valfa5), CD4 and CFSE dilution of the Tg CD4 T cells was analysed. Additionally, cells were co-stained for FoxP3 (after fix and permeabilisation) and the amount of FoxP3+ CFSE+ TCR Tg T-cells was determined after i.v. injection of antigen (C). The adoptively transferred CD4+ T-cell population contained 99% CD25− T cells, indicating that no naturally occurring CD4+ CD25+ Treg was transferred (D). One representative experiment out of two is shown. P-value <0.05 was considered significantly different from responses to native OVA.

FIG. 7: Injection of Sia-OVA prevents the generation of effector cells in-vivo. To examine the strength of Sia-OVA induced tolerance in-vivo, C57BL/6 mice were injected with 100 ug Sia-OVA i.v. Control mice were injected with 100 ug native OVA. One week later, mice were sensitized by injection with 200 ug OVA/25 ug antiCD40 and 50 ug poly I:C. Another week later, mice were sacrificed, spleens were isolated and evaluated for the presence of $FoxP3^+$ T cells, either after fixating, permeabilisation and staining for CD4 and FoxP3 (A. Left panel) or by RT-PCR after RNA isolation (A, right panel). In addition, splenocyted were restimulated for 5 h with OVA 257-264 in the presence of BrefeldinA, cells were harvested, fixed and permeabilised and stained for CD4 and IFNγ (B, left panel). In addition, the presence of IFNγ in culture supernatants was analysed by ELISA (B, right panel). Additionally, spleen cells were restimulated for 24 h with OVA 265-279; BrefeldinA was present during the last 6 hours. Cells were harvested, fixed and permeabilised and stained for CD4 and IFNγ (C), or IL10 (D, left panel). The presence of IL10 in culture supernatants was also analysed by ELISA in cultures that didnot contain BrefeldinA (D, right panel). One representative experiment out of three is shown. Responses were compared with non-treated naive mice. P-value <0.05 was considered significantly different from responses to native OVA.

Figure 8:
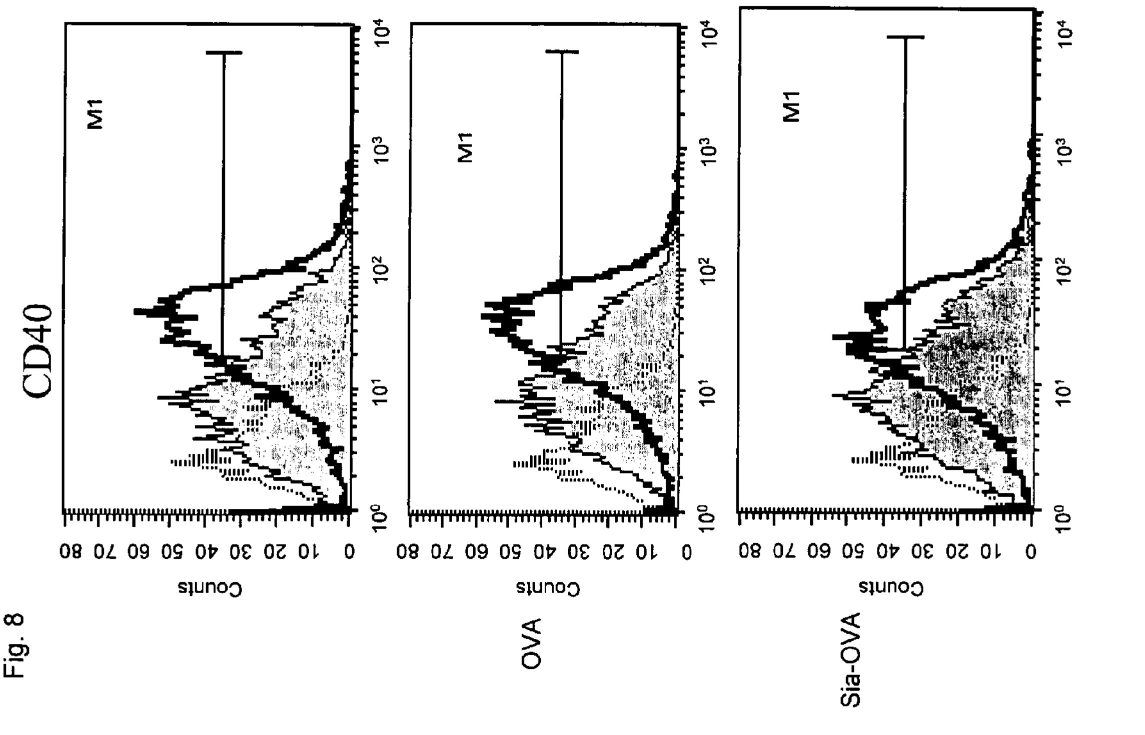

FIG. 8: Low CD40 expression on DC loaded with Sia-OVA. BMDC were incubated with Sia-OVA or native OVA in the absence or presence of LPS. Control DC were incubated with medium or LPS. 24 h later, cells were stained with anti-CD40 and CD11c antibodies and expression of CD40 on CD11c+ DC was analysed using flow cytometry.

EXAMPLES

Example 1

Mice

C57BL/6 mice were purchased from Charles River Laboratories and used at 8-12 weeks of age. OT-I and OT-II TCR transgenic mice were bred and kept in our animal facility under specific pathogen-free conditions. All experiments were approved by the Animal Experiments Committee of the VUmc.

Example 2

Bone Marrow-Derived DC

BMDC were cultured as previously described by Lutz et. al. J.I. Methods 223, 77-92,1999) with minor modifications. Femur and tibia of mice were removed, both ends were cut and the marrow was flushed with Iscove's Modified Dulbecco's Medium (IMDM; Gibco, CA, USA). The resulting marrow suspension was passed over 100 μm gauze to obtain a single cell suspension. After washing, 2×106 cells were seeded per 100 mm dish (Greiner Bio-One, Alphen aan de Rijn, The Netherlands) in 10 ml IMDM, supplemented with 10% FCS; 2 mM L-glutamine, 50 U/ml penicillin, 50 ug/ml streptomycin (BioWhittaker, Walkersville, Md.) and 50 μM β-mercaptoethanol (Merck, Damstadt, Germany) (=IMDMc) and containing 30 ng/ml recombinant murine GM-CSF (rmGM-CSF). At day 2, 10 ml medium containing 30 ng/ml rmGM-CSF was added. At day 5 another 30 ng/ml rmGM-CSF was added to each plate. From day 6 onwards, the non-adherent DC were harvested and used for subsequent experiments.

Example 3

Antibodies

Unconjugated mouse anti-chicken egg albumin (OVA) antibody (OVA-14) was purchased from Sigma Aldrich. FITC-labeled antibodies used were anti-CD11c (clone N418) and anti-CD4 (clone GK1.5).

PE-labeled antibodies were anti-IL-4 (clone 11B11), anti-IL-17 (clone eBioTC11-18H10.1), anti-CD40 (clone MR1), anti-CD80 (clone 16-10-A1), anti-CD86 (clone GL-1), anti-MHC class-II (clone ?,-. APC-labeled antibodies used were anti-CD11c (clone N418), anti-IFNγ (clone XMG1.2) and anti-FoxP3 (clone FJK-16s). All antibodies were purchased from e-Bioscience (Belgium) or BD Biosciences (Belgium)).

Secondary antibodies used in this study were peroxidase-labeled goat anti-human IgG and goat anti-mouse IgG (Jackson, West grove, Pa., USA).

Example 4

Generation of sia-2,3-OVA

3'-Sialyllactose (Neu5Acα2-3Galβ1-4Glc; Dextra labs, UK) was conjugated to Ovalbumin (Calbiochem, Darmstadt, Germany) creating OVA-sia-2,3 using a bifunctional cross linker (4-N-Maleimidophenyl butyric acid hydrazide; MPBH; Pierce, Rockford, USA). In short, via reductive amination, the hydrazide moiety of the linker is covalently linked to the reducing end of the carbohydrate. Hereto, the mixtures were incubated for 2 h at 70°° C. After cooling down to RT, 1 ml ice-cold isopropanol (HPLC grade; Riedel de Haan, Seelze, Germany) was added and the mixture was further incubated at −20° C. for 1 h. Subsequently, the precipitated derivatised carbohydrates were pelleted and dissolved in 1 mM HCl. Ovalbumin was added to derivatised carbohydrates at a 1:10 molar ratio (OVA:carbohydrate) and conjugation was performed o/n at 4° C. The neo-glycoconjugate was separated from reaction-reductants using a PD-10 desalting column (Pierce, Rockford, USA). The concentration of OVA was determined using the bicinchoninic acid assay (Pierce, Rockford, Ill.). Potential endotoxin contamination was determined using a chromogenic LAL endotoxin assay kit (fabrikant). Both OVA-sia2,3 and native OVA were devoid of any endotoxin (Supplemental FIG. 1A).

Additionally, a Dylight 549-N-hydroxysuccimide (NHS) label (Thermo Scientific, Rockford, USA) was covalently coupled to OVA or OVA-sia-2,3 (Dylight-549-OVA). Free label was removed using a PD-10 column (Pierce).

Presence of sia-2,3 on OVA was measured by ELISA. In brief, OVA-sia-2,3 was coated directly onto ELISA plates (NUNC Maxisorb, Roskilde, Denmark) and binding of the plant lectin Maackia amurensis (MAA, Vector Laboratories Inc) was determined as described {Singh, 2010 90/id}, data are shown in Supplemental FIG. 1B.

Example 5

Binding/Uptake Assays $5\times10^4$ BMDC were plated in 96 well round-bottom plates and Dylight 549-labeled antigen (30 μg/ml) was added. Cells were incubated with antigen for 30 min at 4° C. to determine binding, or 1, 2 and 4 h at 37° C. to determine binding/uptake.

MHC Class I and Class II-Restricted Antigen-Presentation Assay

BMDC ($2.5\times10^4$/well) were incubated with indicated concentrations of antigen in 96-well round bottom plates for four hours. After washing, either $5\times10^4$ purified OVA-specific CD4+ or CD8+ T-cells were added to each well. OVA-specific CD4+ and CD8+ T-cells were isolated from lymphoid tissue of OT-I or OT-II mice, respectively. In brief, lymph nodes and spleen were collected and single cell suspensions were obtained by straining the spleens and lymph nodes through a 100 μm gauze. Erythrocytes were depleted by incubation in ACK-lysis buffer and CD4+ or CD8+ T-cells were isolated from the single cell suspensions using the Dynal mouse CD4 or CD8 negative isolation kit (Invitrogen, CA, USA) according to the manufacturer's protocol. Proliferation was assessed by [3H]-thymidine incorporation. [3H]-thymidine (1 μC/well; Amersham Biosciences, NJ, USA) was added for the last 16 h of a 3 day culture. Cells were harvested onto filters and [3H]-thymidine incorporation was assessed using a Wallac microbeta counter (Perkin-Elmer, USA).

Example 6

In-vitro CD4+ Thelper Differentiation Assay $10^4$ BMDC were incubated with 30 μg/ml neo-glycoconjugate or native OVA for 4 h in 96-wells round bottom plates. After washing, 5×104 purified naive CD4+CD62LhiCD25− T-cells isolated from OT-II mice were added to each well. On day 2, 10 IU rmlL-2 was added. On day 7, expression of FoxP3 was analysed using the FoxP3 staining kit (e-Bioscience). Addionally, the frequency of IFNg+, IL4+ or IL17A+ T-cells was determined by intracellular staining. Hereto, T-cells were activated with PMA and ionomycin (100 ng/ml and 1 μg/ml; Sigma) for 6h in the presence of Brefeldin A (Sigma). Cells were co-stained for CD4 and analyzed using a FACScalibur.

Example 7 cDNA Synthesis and Real Time PCR mRNA was isolated by capturing poly(A+)RNA in streptavidin-coated tubes using a mRNA Capture kit (Roche, Basel, Switzerland). cDNA was synthesized using the Reverse Transcription System kit (Promega, WI, USA) following manufacturers guidelines. Real time PCR reactions were performed using the SYBR Green method in an ABI 7900HT sequence detection system (Applied Biosystems).

Example 8

In-vitro Analysis of Treq Induction

Loading of ex-vivo isolated splenic DC with Sia-OVA in-vitro results in generation of tolerogenic DC that induce naïve $CD4^+$ Thelper differentiation towards Treg lineage $10^4$ BMDC were incubated with 30 μg/ml Sia-OVA or native OVA for 4 h in 96-wells round bottom plates. After washing, 5×104 purified naive $CD4^+CD62L^{hi}CD25^-$ T-cells isolated from secondary lymphoid tissue of OT-II Tg mice were added to each well. On day 2, 10 IU rmlL-2 was added. On day 7, expression of FoxP3 was analyzed using a FoxP3 staining kit (e-Bioscience). Additionally, the frequency of $IFN\gamma^+$, $IL4^+$ and $IL17A^+$ T-cells was determined by intracellular staining. Hereto, T-cells were activated with PMA and ionomycin (100 ng/ml and 1 μg/ml; Sigma) for 6 h in the presence of Brefeldin A (Sigma). Cells were co-stained for CD4 and analyzed using a FACScalibur.

We observed that also incubation of naïve OVA-specific $CD4^+$ T-cells with ex-vivo isolated and Sia-OVA loaded splenic DC results in generation of increased numbers of FoxP3+ CD4+ T-cells compared to native OVA-loaded DC (FIG. 4A). Hardly any IFNγ-producing T-cells were detected (FIG. 4B). Neither IL4- nor IL17-producing T-cells were detected in T-cells primed by SIA-OVA or native OVA-loaded DC (not shown).

The induced $FoxP3^+$ T cells were tested for their suppressive capacities. Hereto, they were added to co-cultures of naïve CD4+ OT-II responder T-cells and OVA-loaded DC. By labeling the responder T cells with CFSE, their proliferation can be analyzed via flow cytometry. Only T-cells primed by Sia-OVA-loaded DC suppressed the proliferation of responder T cells (FIG. 4C). T-cells primed by OVA-loaded DC or naïve T cells did not affect the proliferation of the responder T cells.

Figure 5A:
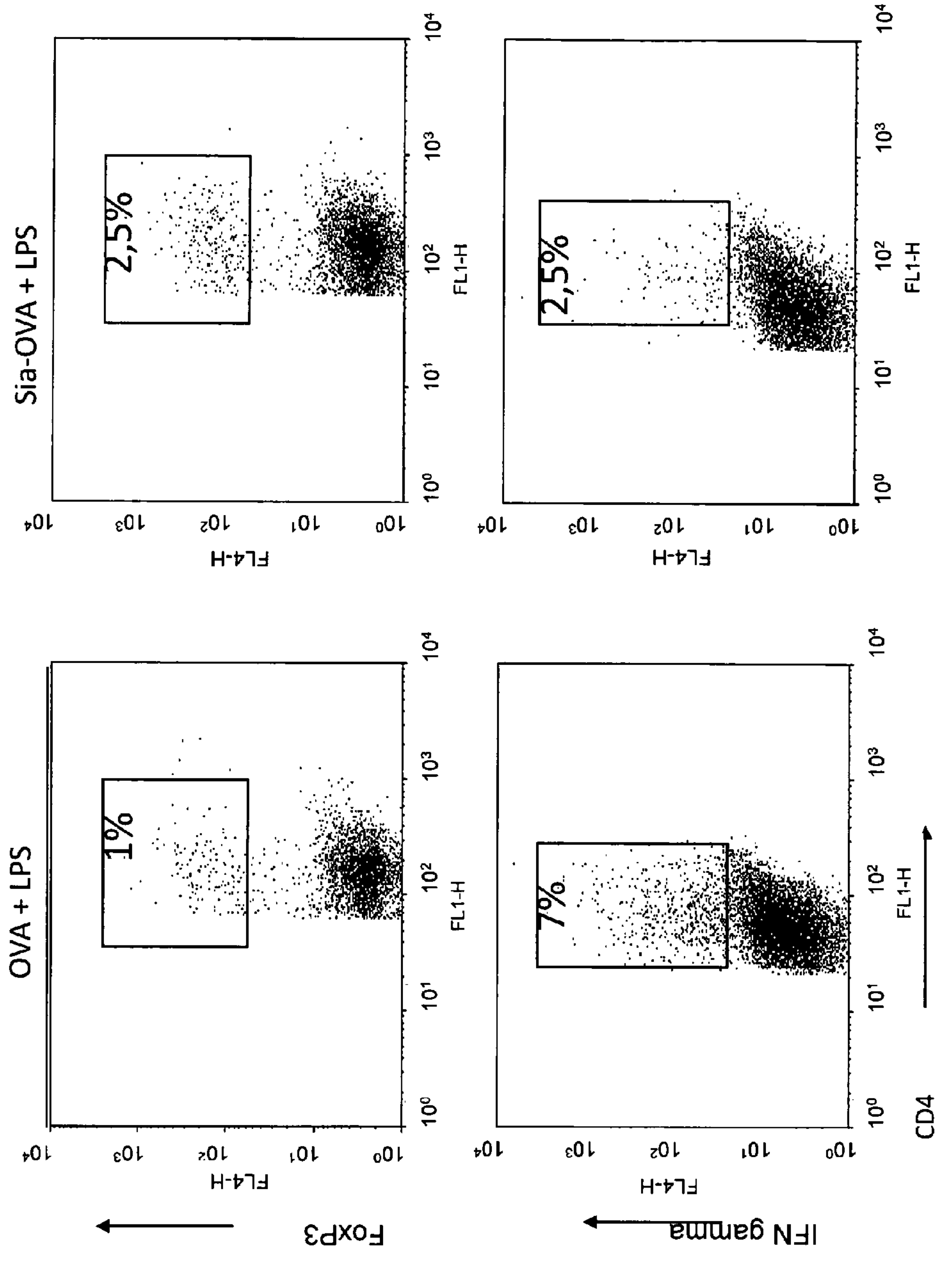
Figure 5B:
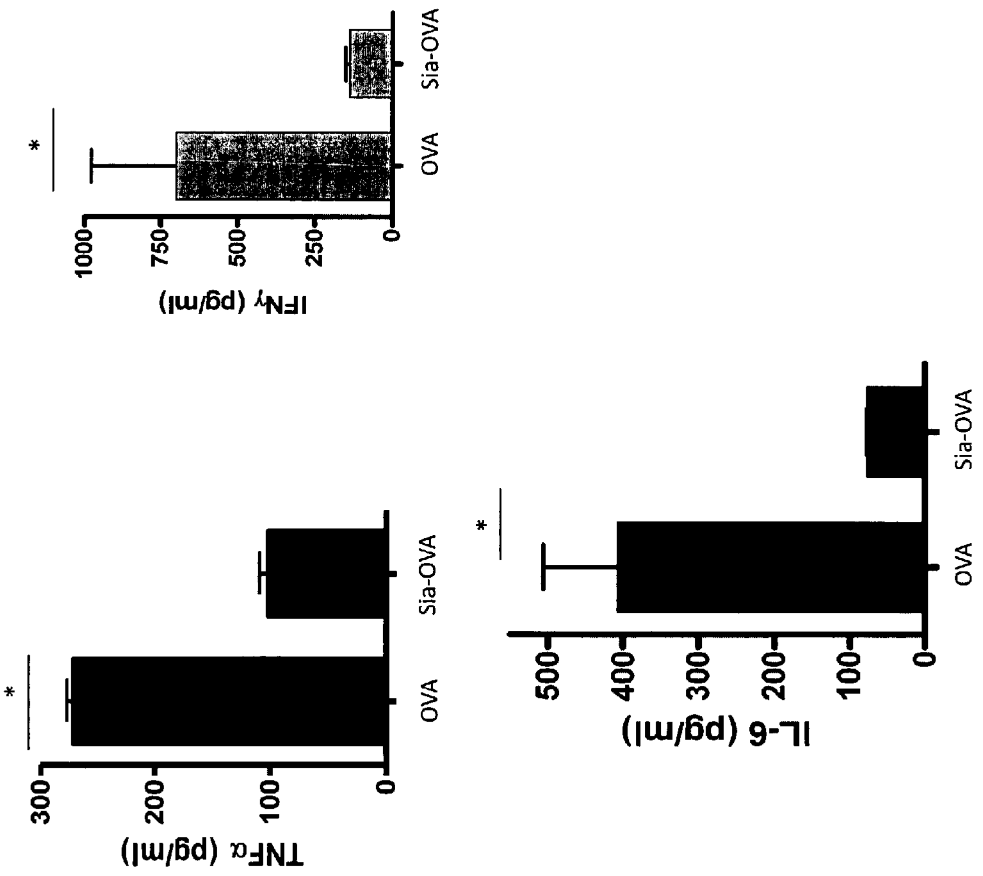

To assess the strength of DC modulation by SIA-OVA uptake (and thus the applicability of administration of sialylated antigens in patients with ongoing immune responses), we loaded ex-vivo isolated splenic DC with Sia-OVA in the presence of LPS (100 ng/ml). Even in this setting, $FoxP3^+$ T-cell generation was detected. Moreover, whereas OVA-LPS loaded DC induced IFNγ production in OVA-reactive T cells, this was not observed in cultures with Sia-OVA-LPS loaded DC (FIG. 5A). Analysis of culture supernatants showed reduced TNFα, IFNγ and IL6 concentrations than culture supernatants from T cells and DC-OVA-LPS (FIG. 5B).

Example 9

In vivo Experiments

The potency of sialylated antigens to induce tolerance in-vivo was analyzed in different models.

Figure 6B:
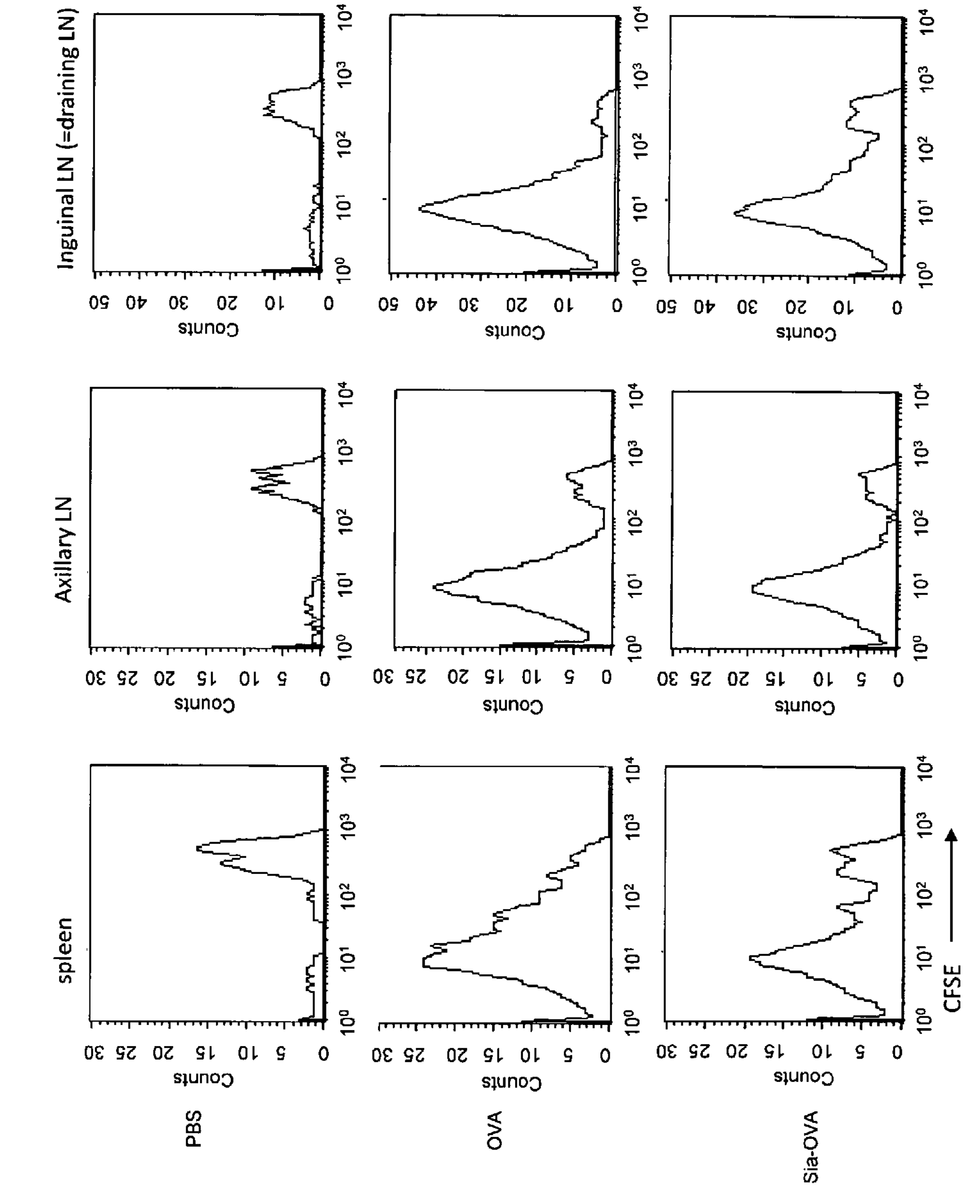
Figure 6C:
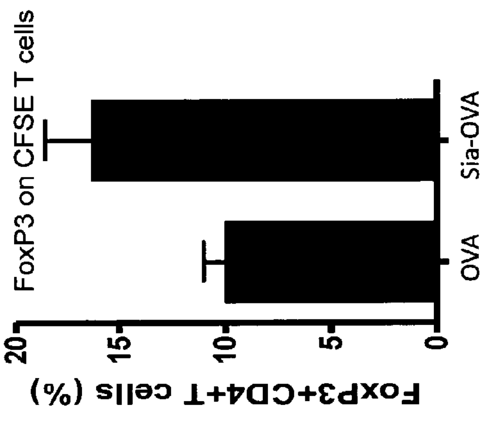
Figure 6D:
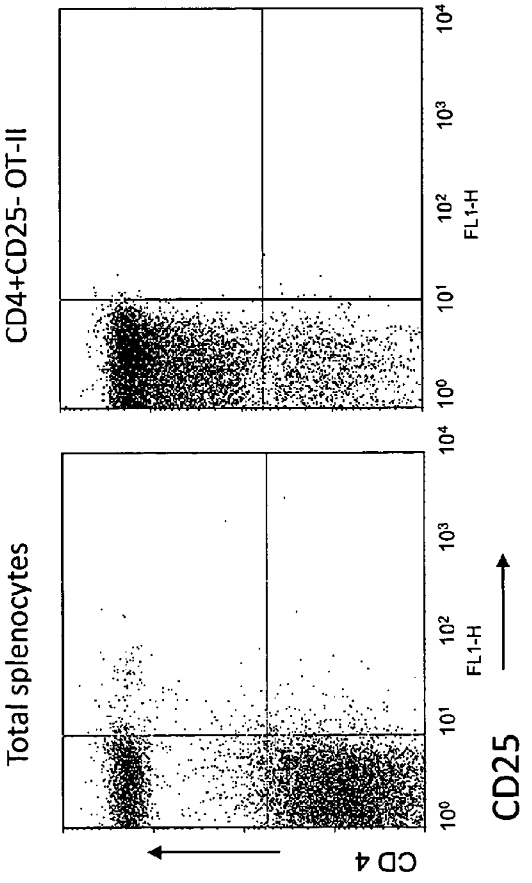

C57BL/6 mice were adoptively transferred with CFSE-labeled CD4+ OT-II T-cells. One day later, mice were injected with 100 μg OVA-SIA or native OVA i.v.

or s.c. and three days later, lymphoid tissues were analyzed for the proliferation of the transferred OVA-specific CD4 T-cells. Control mice received PBS, which did not lead to proliferation of the transferred CD4 T-cells (FIG. 6A). We observed that injection of OVA induced massive proliferation (FIG. 6A), irrespective of site used for injection (i.v. or s.c.). However, i.v. injection of Sia-OVA resulted in reduced proliferation of the transferred OT-II T cells. The reduction in proliferation was observed systemically (spleen and lymph nodes). Injection of Sia-OVA s.c. did not show prominent effects on OT-II T cell proliferation in the draining lymph nodes compared to OVA (FIG. 6B). When analyzing the phenotype of the transferred OT-II T cells we observed that only in the Sia-OVA injected mice, the T cells were positive for FoxP3 (FIG. 6C). Since the injected OT-II T-cells were $CD25^-CD4^+$ T cells, thus devoid of $CD25^+CD4^+$ naturally occurring Treg, these data show that injection of Sia-OVA results in de novo induction of FoxP3+ Treg (FIG. 6D).

Furthermore, these data suggest that the receptor for Sia is mostly present on antigen presenting cells, in particular on DC in the spleen.

Figure 7A:
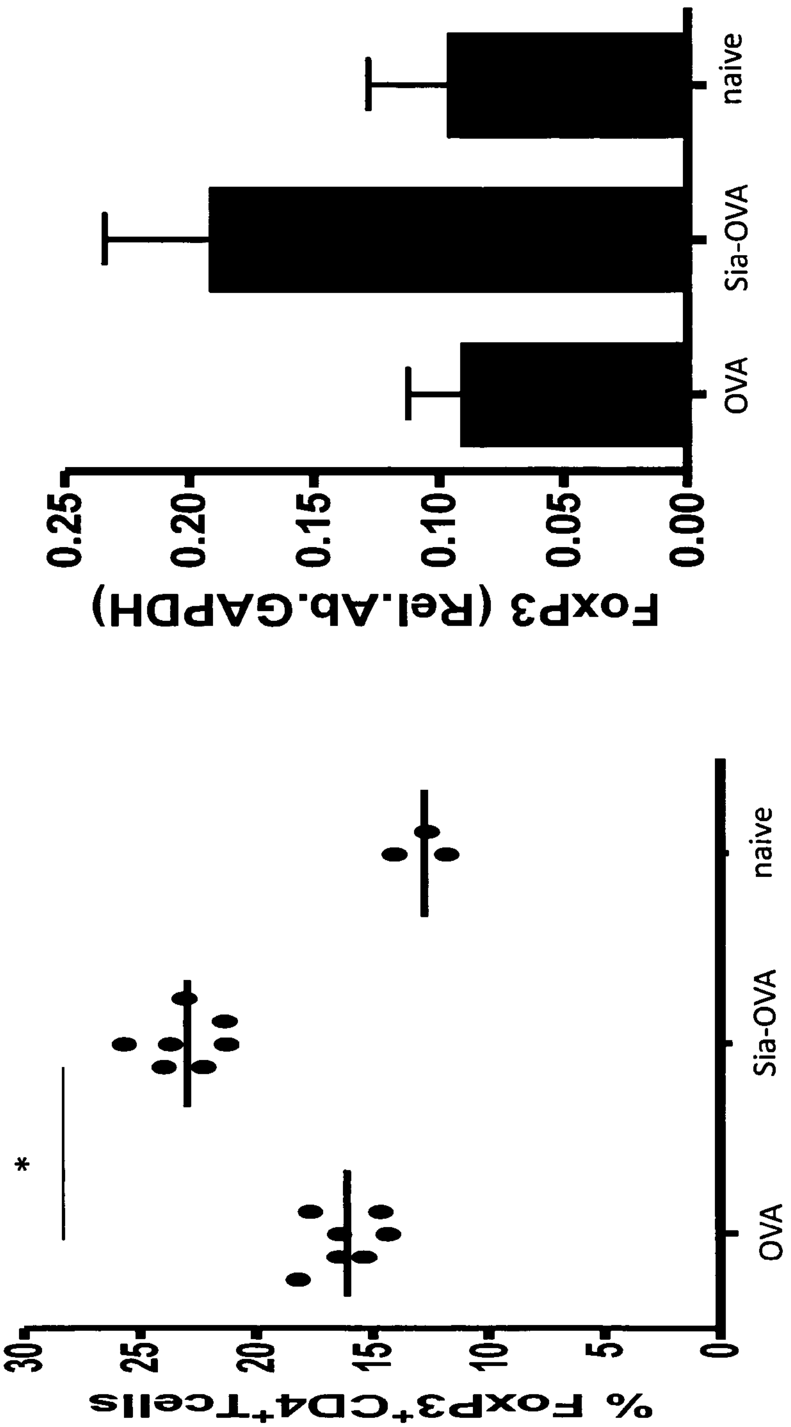

Since i.v. injection of Sia-OVA had such prominent effects on $FoxP3^+$ T cell generation in-vivo, we assessed whether these cells could prevent the generation of effector T cells. Hereto, C57BL/6 mice were treated with Sia-OVA before immunization. This group was compared with mice treated with OVA. Mice were immunized one week later by i.v. injection of 100 μg OVA mixed with 25 μg aCD40 and poly I:C. One week after immunization, spleens were collected and the frequency of $FoxP3^+$ $CD4^+$ T cells was analyzed by flow cytometry. Compared to naïve control mice, there was a significant increase in the percentage of $FoxP3^+$ T-cells detected in the spleens of Sia-OVA but not native OVA treated mice. This was also significantly higher than the percentage detected in spleens of native OVA treated mice (FIG. 7A left panel), which was confirmed by RT-PCR on total splenocytes (FIG. 7A right panel).

Figure 7B:
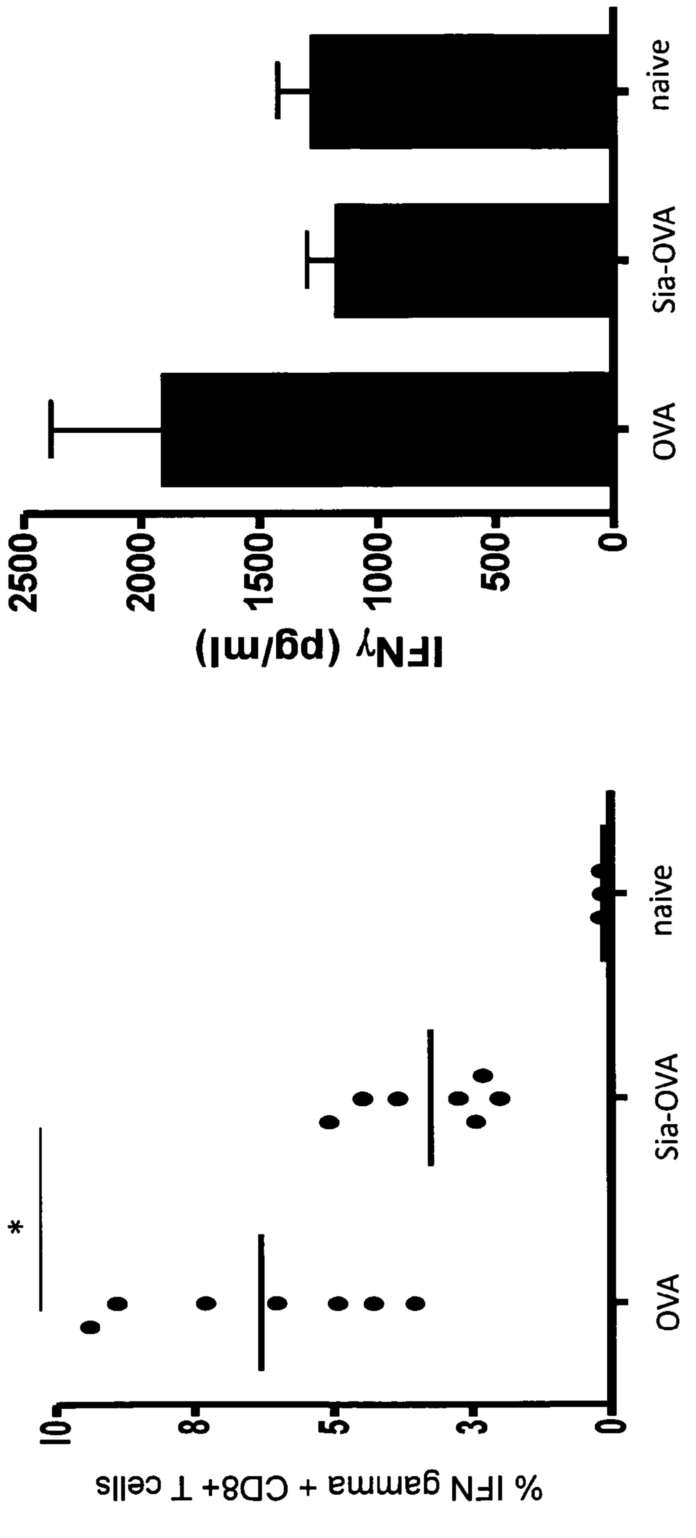

In addition, the presence of CD8 and CD4 effector T cells was determined upon in-vitro re-stimulation with OVA peptides ($OVA_{257-264}$ and $OVA_{265-279}$, respectively) and intracellular cytokine staining. The percentage of IFNγ-producing CD8 T-cells was significantly reduced in Sia-OVA treated mice compared to OVA treated mice (FIG. 7B, left). This was confirmed when measuring IFNγ levels in the supernatant of parallel cultures (FIG. 7B, right). Analysis of IFNg production by CD4 T cells did not show significant differences (FIG. 7C). This may be due to the fact that induced Treg have been shown to produce IFNγ as well (e.g. Tr1 cells). Hereto, simultaneous analysis for IL10 should be performed in future to discriminate these IL10 and IFNγ-producing Treg from IFNγ-producing effector T cells.

Analysis of IL10-producing CD4 T-cells showed that there was a significantly increased percentage of IL10-secreting T cells in the spleens of SIA-OVA treated mice. However, this was not significantly different from the percentage that was found in spleens of native OVA treated mice (FIG. 7D, left). These data were confirmed when analyzing the supernatants of splenocytes after o/n culture (FIG. 7D, right).

Furthermore, our experiments clearly showed that when we injected DC in vitro loaded with SIA-OVA into C57BL/6 mice, followed by a challenge with OVA+CpG, we observed a strong induction of FoxP3+Treg and a decrease of effector CD4 T-cell induction. This clearly shows that induction of tolerance in vivo is mediated by DC.

Example 10

Modulation of DC

We have analysed the phenotype of DC after taking up Sia-OVA and compared it with the phenotype of DC that ingested native OVA. This was done in both the absence and presence of LPS. It was shown that CD40 is consistently lower on Sia-OVA loaded DC when compared to OVA loaded DC.

To get more insight in the underlying mechanism of tolerance induction by Sia-OVA loaded DC, we performed a micro-array analysis. Hereto, DC were incubated with 50 μg/ml Sia-OVA or native OVA and 1 and 6 h later, DC were harvested and RNA was extracted using the nucleospin kit. Genomic DNA was removed using DNAse treatment. RNA quality and integrity was checked by Service XS (Leiden). Based on good quality, RNA was amplified, labeled and hybridized on BeadChip Arrays (MouseWG-6 v2, Illumina). We have compared the normalized gene expression of Sia-OVA DC with OVA-DC and all samples that show more than 10-fold differences (higher or lower) are in Table 2. Most interesting genes seem AIRE (higher in Sia-OVA DC) and the switching on of a type I IFN pathway. Both have been related to tolerance and also seem to be connected with each other.

TABLE 2

| | | OVA-sa2,3 vs OVA 1 h | OVA-sa2,3 vs OVA 6 h | OVA-sa2,6 vs OVA 1 h | OVA-sa2,6 vs OVA 6 h |
|---|---|---|---|---|---|
| ILMN_2659408 | Rel | 1,028345 | 1,103712 | 0,103688 | 11,1404 |
| ILMN_1249750 | Reln | 0,101298 | 0,101936 | 0,999407 | 102,914 |
| ILMN_2674533 | Renbp | 99,51158 | 0,986405 | 97,55804 | 0,978967 |
| ILMN_2641270 | AA536717 | 0,098526 | 10,40813 | 0,995059 | 98,62595 |
| ILMN_2605630 | AA881470 | 101,2935 | 0,977818 | 98,89889 | 0,96501 |
| ILMN_2719139 | AB124611 | 98,90014 | 0,098043 | 100,2287 | 0,930972 |
| ILMN_1218537 | Abca15 | 102,7413 | 1,008956 | 100,6122 | 9,991803 |
| ILMN_2663015 | Abcb8 | 1,024122 | 0,100682 | 0,099732 | 100,361 |
| ILMN_2685157 | Abcc3 | 999,247 | 0,930306 | 1001,941 | 0,938589 |
| ILMN_1253491 | Abcc9 | 1,006649 | 0,959709 | 1,002382 | 102,7102 |
| ILMN_2687062 | Abr | 99,01085 | 0,997722 | 98,67048 | 0,9895 |
| ILMN_2739219 | Acad10 | 1020,163 | 0,964181 | 1012,151 | 0,984681 |
| ILMN_1220016 | Acbd5 | 0,984563 | 0,991942 | 0,099628 | 98,83858 |
| ILMN_2770667 | Acin1 | 0,979681 | 0,097175 | 0,946506 | 99,56963 |
| ILMN_1216022 | Aclp7 | 1,00318 | 10,64468 | 10,17214 | 104,08 |
| ILMN_2745889 | Acot2 | 0,980553 | 9,743136 | 0,977466 | 95,41733 |
| ILMN_1213138 | Acy1 | 97,356 | 0,952368 | 99,73741 | 0,965828 |
| ILMN_3139103 | Adam15 | 0,099838 | 8,929052 | 1,004738 | 87,97479 |
| ILMN_1240629 | Adam15 | 104,2488 | 0,967151 | 102,0592 | 0,094326 |
| ILMN_3134632 | Adam22 | 102,1393 | 10,06842 | 100,5282 | 1,016651 |

TABLE 2-continued

| | | OVA-sa2,3 vs OVA 1 h | OVA-sa2,3 vs OVA 6 h | OVA-sa2,6 vs OVA 1 h | OVA-sa2,6 vs OVA 6 h |
|---|---|---|---|---|---|
| ILMN_3033533 | Add1 | 1,00665 | 9,572825 | 1,012456 | 93,49712 |
| ILMN_2738082 | Adipoq | 0,993226 | 0,096595 | 0,995041 | 99,89807 |
| ILMN_1215394 | Adpgk | 10,10091 | 99,35876 | 9,956478 | 0,991647 |
| ILMN_1215901 | Agpat2 | 10,13781 | 1,05875 | 97,95148 | 1,041015 |
| ILMN_2972521 | Agtr1a | 0,09689 | 1,010311 | 0,974424 | 102,1489 |
| ILMN_2590950 | Agtrap | 9,612647 | 103,6355 | 0,009756 | 0,102844 |
| ILMN_2916008 | Agxt2l2 | 0,972468 | 99,42319 | 0,950237 | 0,993325 |
| ILMN_1258578 | Ahnak | 1,038872 | 9,531327 | 0,105231 | 95,0189 |
| ILMN_2684007 | AI844366 | 0,997183 | 1,013509 | 1,013799 | 99,31121 |
| ILMN_1216550 | AI851790 | 0,993945 | 0,998739 | 0,989183 | 100,3487 |
| ILMN_2673099 | A1987944 | 0,98241 | 1,018939 | 0,996969 | 101,1484 |
| ILMN_1213787 | Aire | 1,026076 | 0,998319 | 1,012772 | 100,1469 |
| ILMN_1235909 | Ak2 | 9,870461 | 0,109321 | 97,77247 | 1,08545 |
| ILMN_1246068 | Akap12 | 100,2487 | 0,102842 | 101,4649 | 1,049984 |
| ILMN_3116504 | Akap2 | 0,100643 | 1,09025 | 0,09927 | 105,2205 |
| ILMN_2627299 | Akap9 | 1,040274 | 95,7044 | 0,987936 | 9,503727 |
| ILMN_2661287 | Akp2 | 0,991037 | 0,102454 | 0,97956 | 98,13207 |
| ILMN_2481458 | Akr1b3 | 99,68519 | 0,975054 | 99,46308 | 1034,701 |
| ILMN_1214358 | Akt1s1 | 1,017785 | 103,7958 | 10,22891 | 1,061528 |
| ILMN_3100276 | Aldh1l1 | 10,07558 | 0,980369 | 100,8811 | 0,984862 |
| ILMN_1224012 | Aldob | 9,665992 | 0,985546 | 97,35459 | 0,100766 |
| ILMN_2660414 | Alg5 | 99,73186 | 1,018703 | 101,2032 | 0,098715 |
| ILMN_2892292 | Alg9 | 1,011797 | 1,011511 | 1,016208 | 102,1624 |
| ILMN_1235966 | Alox12b | 99,32697 | 1,023599 | 100,3686 | 101,8012 |
| ILMN_2681123 | Als2cr2 | 976,0651 | 0,960205 | 1005,91 | 0,091872 |
| ILMN_2718293 | Amelx | 99,37019 | 9,926122 | 101,5065 | 0,975022 |
| ILMN_2859778 | Anapc4 | 0,971498 | 0,977219 | 1,006495 | 100,3286 |
| ILMN_2568390 | Angptl3 | 0,977892 | 0,097669 | 0,999894 | 974,3339 |
| ILMN_1253761 | Ankrd39 | 9,849003 | 96,10191 | 10,3044 | 0,95381 |
| ILMN_2592358 | Ankrd49 | 0,970275 | 0,977431 | 0,918654 | 101,763 |
| ILMN_1217993 | Ankrd6 | 1,012684 | 99,42222 | 0,974492 | 0,992855 |
| ILMN_2665496 | Ankrd9 | 102,6115 | 1,01209 | 100,6919 | 1,022893 |
| ILMN_2735877 | Anks3 | 103,0724 | 0,910252 | 103,0553 | 8,992366 |
| ILMN_2685507 | Anp32a | 0,098381 | 0,953522 | 1,016315 | 94,34225 |
| ILMN_1230010 | Anxa10 | 9,946819 | 101,7208 | 9,982971 | 1,031209 |
| ILMN_1219115 | Apc | 0,987325 | 98,93451 | 0,961718 | 0,992878 |
| ILMN_2449193 | Apg4d | 97,58354 | 0,099454 | 97,66596 | 0,986757 |
| ILMN_1232821 | Aph1a | 102,3822 | 0,995923 | 10,24009 | 100,4748 |
| ILMN_2916782 | Apom | 0,988538 | 0,893169 | 0,97074 | 86,82716 |
| ILMN_2724868 | Appbp2 | 96,78724 | 1,000733 | 92,39066 | 10,28014 |
| ILMN_1225901 | Aqp11 | 0,998861 | 0,995061 | 1,005773 | 96,73764 |
| ILMN_2943165 | Aqp7 | 0,097988 | 0,996017 | 0,990391 | 995,3483 |
| ILMN_1237241 | Araf | 10,37345 | 96,13192 | 10,44231 | 0,096285 |
| ILMN_2649846 | Arcn1 | 103,324 | 0,963489 | 10,08846 | 0,098458 |
| ILMN_2743425 | Arfip1 | 10,03356 | 0,961122 | 100,2037 | 0,935154 |
| ILMN_2613531 | Arhgap21 | 1,003831 | 0,981488 | 0,980804 | 96,2602 |
| ILMN_2589999 | Arl10c | 0,985403 | 89,7199 | 0,975282 | 8,821913 |
| ILMN_3066763 | Arl4a | 104,433 | 1,050157 | 103,2892 | 1,022906 |
| ILMN_1247625 | Arp3b-pending | 1,006938 | 0,971162 | 1,001264 | 964,7989 |
| ILMN_2666279 | Arrdc3 | 1,077088 | 0,086627 | 1,058399 | 897,2452 |
| ILMN_2679609 | Art1 | 0,101671 | 9,850694 | 1,014597 | 101,1813 |
| ILMN_2629591 | Asah1 | 105,1951 | 0,118185 | 10,55519 | 1,141375 |
| ILMN_2663555 | Asb3 | 101,6378 | 1,13001 | 9,793706 | 1,121915 |
| ILMN_3075168 | Ash2l | 0,969681 | 0,098741 | 1,00595 | 100,8362 |
| ILMN_3006123 | Asns | 96,1865 | 1,016376 | 98,12903 | 0,968906 |
| ILMN_2776700 | Asph | 10,012 | 101,4094 | 10,22624 | 0,999028 |
| ILMN_2594584 | Asph | 100,5377 | 9,837391 | 98,59214 | 0,101903 |
| ILMN_2629103 | Atcay | 10,20191 | 0,977784 | 9,779767 | 99,57801 |
| ILMN_2620574 | Atg16l1 | 982,569 | 9,468761 | 101,9885 | 0,967669 |
| ILMN_2606567 | Atic | 97,46479 | 0,963219 | 99,36086 | 1,006792 |
| ILMN_1258206 | Atm | 99,02622 | 0,977615 | 9,747839 | 1,012082 |
| ILMN_3038944 | Atp2b2 | 1,032362 | 1011,428 | 0,980498 | 0,999334 |
| ILMN_2973897 | Atp5l | 95,48242 | 1,000159 | 97,48098 | 0,994841 |
| ILMN_2680440 | Atp6v1b2 | 99,90241 | 0,953126 | 100,8208 | 0,9605 |
| ILMN_2755322 | Atp6v1e2 | 101,832 | 0,994822 | 99,59874 | 1,0165 |
| ILMN_1255220 | Atp9a | 0,100331 | 10,10136 | 1,008405 | 101,7454 |
| ILMN_1229377 | AU017455 | 0,955379 | 992,8015 | 0,94251 | 0,998757 |
| ILMN_2919343 | Aven | 97,77753 | 1,005044 | 99,18759 | 10,18624 |
| ILMN_2755585 | Avpi1 | 1,012887 | 1,08022 | 1,030473 | 110,9546 |
| ILMN_1251934 | Azi2 | 101,4731 | 9,879583 | 99,25178 | 9,993418 |
| ILMN_1247168 | B130032G09Rik | 9,890892 | 10,15862 | 100,8566 | 1,005667 |
| ILMN_1257672 | B230205M18 | 1,005101 | 0,999803 | 1,014716 | 97,46832 |
| ILMN_2565428 | B230325K09Rik | 9,968016 | 0,983847 | 9,758051 | 995,26 |
| ILMN_1235144 | B230399H06Rik | 101,9651 | 0,102365 | 100,7778 | 1,012485 |
| ILMN_2669708 | B3gat2 | 1011,864 | 0,98462 | 1008,746 | 1,014485 |

TABLE 2-continued

| | | OVA-sa2,3 vs OVA 1 h | OVA-sa2,3 vs OVA 6 h | OVA-sa2,6 vs OVA 1 h | OVA-sa2,6 vs OVA 6 h |
|---|---|---|---|---|---|
| ILMN_3149776 | B3gnt8 | 10,06867 | 90,3311 | 103,1875 | 0,91006 |
| ILMN_1216802 | Bad | 0,102461 | 0,957779 | 0,009748 | 94,21028 |
| ILMN_2665609 | Baiap2l1 | 988,7948 | 1,024328 | 976,3332 | 0,999748 |
| ILMN_2749866 | Bap1 | 9,676667 | 0,959977 | 0,973136 | 95,05828 |
| ILMN_2652385 | Baz2a | 1,000717 | 9,973698 | 0,964416 | 98,74386 |
| ILMN_2684272 | Bbs9 | 102,191 | 1,011412 | 101,3924 | 9,963482 |
| ILMN_3006534 | BC003885 | 99,0739 | 1,03535 | 101,7832 | 1,02412 |
| ILMN_3133238 | BC013491 | 99,14106 | 0,990603 | 97,97291 | 1,035456 |
| ILMN_2688176 | BC046418 | 0,983674 | 0,985768 | 1,005455 | 96,46881 |
| ILMN_2960128 | BC048502 | 0,099621 | 0,979413 | 0,992124 | 100,9488 |
| ILMN_2664291 | BC055111 | 99,83961 | 0,099096 | 98,75682 | 0,984474 |
| ILMN_2993962 | BC099439 | 0,981124 | 1033,503 | 0,098784 | 1,026491 |
| ILMN_2677422 | Bcl2l14 | 100,8667 | 0,98433 | 102,2935 | 0,959676 |
| ILMN_2713638 | Bcmo1 | 0,997612 | 0,993911 | 0,992652 | 98,05958 |
| ILMN_2639819 | Bet1l | 9,780487 | 0,998096 | 97,10562 | 0,100206 |
| ILMN_2681241 | Birc5 | 0,102187 | 101,0209 | 0,099758 | 0,98774 |
| ILMN_2910258 | Bnc1 | 1,050197 | 0,978384 | 1,004996 | 103,3005 |
| ILMN_2846368 | Bola2 | 98,00094 | 0,937006 | 97,37207 | 0,930611 |
| ILMN_1253942 | Bop1 | 93,89475 | 10,0153 | 94,85711 | 1,036676 |
| ILMN_1243635 | Brunol4 | 97,2682 | 1,007737 | 98,66806 | 1,014305 |
| ILMN_1224958 | C030015H18 | 98,21568 | 0,09935 | 100,2623 | 0,989865 |
| ILMN_1259185 | C030048B08Rik | 101,1684 | 0,995838 | 102,8585 | 10,23537 |
| ILMN_1233652 | C130015E15Rik | 103,0576 | 1,014571 | 99,38498 | 0,985424 |
| ILMN_2753279 | C130023O10Rik | 96,23538 | 10,02187 | 98,53216 | 1,002206 |
| ILMN_2754119 | C130039O16Rik | 0,976549 | 1,000482 | 0,997887 | 986,9044 |
| ILMN_1223290 | C130046N05Rik | 1,038869 | 0,100686 | 1,016037 | 10044,12 |
| ILMN_1228917 | C330023M02Rik | 0,956375 | 1,032472 | 0,945739 | 1018,341 |
| ILMN_2702286 | Cacnb3 | 1,020904 | 1,150696 | 1,025121 | 114,2253 |
| ILMN_1241128 | Calcoco1 | 996,5213 | 0,089271 | 100,732 | 0,874231 |
| ILMN_1257323 | Car6 | 1,012838 | 0,978974 | 0,989067 | 1002,46 |
| ILMN_2866175 | Card14 | 9,803762 | 10,16014 | 9,931693 | 102,0377 |
| ILMN_1220811 | Caskin1 | 1,014175 | 0,996775 | 1,009265 | 98,46722 |
| ILMN_2865939 | Ccdc100 | 9,960177 | 9,40414 | 10,06811 | 92,64171 |
| ILMN_2745151 | Ccdc123 | 0,098653 | 0,972197 | 0,961661 | 96,12732 |
| ILMN_2756733 | Ccdc130 | 100,0595 | 0,959578 | 99,43568 | 0,951075 |
| ILMN_2671436 | Ccdc77 | 101,2349 | 0,964637 | 96,68356 | 0,988785 |
| ILMN_2752408 | Ccdc90b | 1,007825 | 0,10722 | 0,991932 | 103,8052 |
| ILMN_2862179 | Ccl11 | 98,9178 | 0,982289 | 97,0845 | 0,983082 |
| ILMN_2771176 | Ccl7 | 83,83454 | 0,122139 | 89,36513 | 1,25809 |
| ILMN_2863768 | Ccnb3 | 0,992992 | 0,999488 | 0,988422 | 97,21907 |
| ILMN_2669793 | Ccnd1 | 0,998637 | 0,101775 | 0,966321 | 102,7623 |
| ILMN_3131063 | Ccnd3 | 0,963618 | 8,522801 | 0,098333 | 85,32755 |
| ILMN_2696291 | Cd209d | 100,111 | 0,100882 | 101,6694 | 0,990543 |
| ILMN_2665757 | Cd209e | 0,977415 | 0,100134 | 0,982201 | 9,986747 |
| ILMN_3117602 | Cd6 | 1022,289 | 9,172848 | 1033,979 | 0,091576 |
| ILMN_2586179 | Cd69 | 0,969605 | 1,010149 | 9,560333 | 103,03 |
| ILMN_2731282 | Cd8a | 10,24021 | 1,014975 | 10,22786 | 1016,535 |
| ILMN_1244296 | Cdc14b | 0,101063 | 1,001597 | 1,007298 | 98,53194 |
| ILMN_2612206 | Cdc20 | 1006,605 | 0,93934 | 974,0858 | 9,245129 |
| ILMN_1250900 | Cdk7 | 101,045 | 0,982047 | 985,5148 | 0,956287 |
| ILMN_2732437 | Chrna6 | 1,018822 | 1,05132 | 1,008538 | 995,2643 |
| ILMN_1235663 | Cnot8 | 101,847 | 1,01818 | 102,0317 | 9,862585 |
| ILMN_2589422 | Col6a1 | 0,97806 | 0,984973 | 1,011739 | 97,71503 |
| ILMN_2671689 | Cox7b | 100,9042 | 1,056407 | 100,3663 | 1,022861 |
| ILMN_1236346 | Cpeb2 | 1,0092 | 1,006872 | 1,004107 | 101,0207 |
| ILMN_2877900 | Cpne5 | 0,99407 | 1,018435 | 1,014962 | 102,8263 |
| ILMN_2913078 | Cps1 | 9,861924 | 0,100572 | 9,963818 | 101,7166 |
| ILMN_1213549 | Creb3l4 | 0,95467 | 9995,844 | 9,819902 | 0,983614 |
| ILMN_1216758 | Crem | 101,0591 | 0,992101 | 100,802 | 0,970744 |
| ILMN_1233069 | Crh | 97,64674 | 0,999484 | 1010,487 | 0,986246 |
| ILMN_2907964 | Crim2 | 0,989478 | 0,929252 | 0,99025 | 93,03724 |
| ILMN_2987844 | Crk | 101,1075 | 1,011071 | 101,1205 | 0,993613 |
| ILMN_2668253 | Crkrs | 0,965559 | 1,010495 | 0,099876 | 99,35456 |
| ILMN_2728094 | Cryba1 | 100,1304 | 0,986998 | 100,073 | 1,024256 |
| ILMN_2613659 | Ctdp1 | 94,92608 | 9,832516 | 97,15404 | 0,958597 |
| ILMN_2858769 | Ctps2 | 1,009855 | 0,980505 | 0,99267 | 98,51342 |
| ILMN_1253235 | Cugbp2 | 98,95966 | 0,932621 | 97,68206 | 0,992364 |
| ILMN_2760019 | Cxcl13 | 98,46601 | 1,022856 | 98,65985 | 1,014522 |
| ILMN_2659426 | Cxcl14 | 1,001054 | 0,953478 | 0,997075 | 982,147 |
| ILMN_3078306 | Cyb561d1 | 100,5749 | 0,952014 | 101,5275 | 0,945079 |
| ILMN_1241818 | Cyp2c54 | 10,05082 | 0,994231 | 100,6704 | 1,033107 |
| ILMN_2525402 | D10Bwg1379e | 9968,751 | 0,098971 | 9781,422 | 0,995327 |
| ILMN_2691157 | Dctn1 | 0,986458 | 0,104052 | 0,095007 | 108,3556 |
| ILMN_2446727 | Ddhd1 | 105,4707 | 0,900495 | 103,8381 | 0,09623 |
| ILMN_1259277 | Ddx28 | 0,097655 | 9,727763 | 0,962635 | 953,9783 |

TABLE 2-continued

| | | OVA-sa2,3 vs OVA 1 h | OVA-sa2,3 vs OVA 6 h | OVA-sa2,6 vs OVA 1 h | OVA-sa2,6 vs OVA 6 h |
|---|---|---|---|---|---|
| ILMN_2692412 | Defb2 | 96,91346 | 1,010442 | 97,91363 | 0,996252 |
| ILMN_1229247 | Defb41 | 0,978942 | 1,001083 | 1,014259 | 100,6946 |
| ILMN_2658961 | Dgka | 0,100532 | 1,006368 | 0,1036 | 996,6944 |
| ILMN_3101919 | Dgkh | 0,995508 | 1,000368 | 1,027322 | 96,16117 |
| ILMN_2462151 | Dgkq | 99,91771 | 1,008908 | 100,2425 | 0,984353 |
| ILMN_2915059 | Dgkz | 94,59734 | 8,56831 | 9,67789 | 8,70217 |
| ILMN_1222841 | Dgl1-pending | 97,55169 | 0,989549 | 99,01643 | 1,003833 |
| ILMN_1233008 | Dhx30 | 98,64991 | 0,967717 | 100,4042 | 0,009669 |
| ILMN_2611098 | Dip2b | 100,9192 | 9,737461 | 100,2285 | 0,98252 |
| ILMN_2746556 | Dkk3 | 99,38057 | 0,965588 | 100,6638 | 10,00113 |
| ILMN_2627081 | Dkkl1 | 102,0234 | 0,981478 | 100,266 | 1,000026 |
| ILMN_2914010 | Dmwd | 98,03993 | 9,084114 | 100,2711 | 0,89593 |
| ILMN_2725428 | Dnajb10 | 103,5862 | 1,077698 | 103,9828 | 1,09103 |
| ILMN_2751925 | Dpp3 | 95,03934 | 0,957978 | 95,86784 | 0,936473 |
| ILMN_2677494 | Drg2 | 1,001753 | 1,032778 | 0,998074 | 99,72893 |
| ILMN_2775813 | Dusp12 | 99,66745 | 1,009156 | 95,62582 | 0,978808 |
| ILMN_3053158 | Dyrk1b | 103,1909 | 0,937689 | 106,0038 | 0,927979 |
| ILMN_2572643 | E330034F13Rik | 0,100319 | 10,24731 | 1,010142 | 1041,036 |
| ILMN_2702508 | Ebna1bp2 | 9,687253 | 0,099876 | 97,12832 | 10,03834 |
| ILMN_2861879 | Edar | 1,011165 | 1,00212 | 0,099657 | 95,22979 |
| ILMN_2643355 | Edaradd | 1,00308 | 1,01157 | 0,098737 | 100,847 |
| ILMN_2765015 | Eed | 100,1992 | 0,999645 | 99,85057 | 1,023327 |
| ILMN_3061673 | Eef1d | 997,3336 | 1,015619 | 968,0081 | 0,988045 |
| ILMN_2846821 | EG328280 | 97,56242 | 9,888982 | 97,48851 | 1,009572 |
| ILMN_2493668 | EG330031 | 99,10159 | 10,03361 | 102,1472 | 1,017641 |
| ILMN_1242669 | Egflam | 99,08995 | 0,988674 | 98,23838 | 0,09474 |
| ILMN_2653543 | Egr3 | 98,40926 | 0,995354 | 100,3774 | 0,970772 |
| ILMN_2789601 | Eif3i | 0,993122 | 0,977201 | 0,099271 | 99,0758 |
| ILMN_1243394 | Eif4b | 99,77838 | 0,978956 | 102,0176 | 0,968495 |
| ILMN_1254206 | Eif4e1b | 99,26624 | 1,009229 | 98,58994 | 1,023777 |
| ILMN_2697304 | Eln | 0,998608 | 0,09873 | 0,100388 | 98,20773 |
| ILMN_2614752 | Elovl6 | 97,7495 | 0,939998 | 103,1668 | 0,092278 |
| ILMN_2757062 | ENSMUSG00000033219 | 103,4994 | 9,774745 | 101,3423 | 1,041206 |
| ILMN_1258722 | ENSMUSG00000042857 | 101,8688 | 9,759741 | 100,9402 | 1,000307 |
| ILMN_3129160 | Epas1 | 99,12285 | 0,098759 | 99,41097 | 0,097499 |
| ILMN_2686924 | Epha1 | 98,41166 | 0,99898 | 98,07619 | 10,22057 |
| ILMN_2679830 | Epsti1 | 9,980848 | 1,009307 | 9,849766 | 98,49 |
| ILMN_1250597 | Erbb3 | 101,7993 | 1,007096 | 100,7874 | 1,036176 |
| ILMN_2772035 | Erc1 | 0,947979 | 1,00777 | 0,973254 | 100,2977 |
| ILMN_2992541 | Ergic3 | 10,17137 | 0,097703 | 10,27961 | 95,0453 |
| ILMN_1213296 | Evi5l | 0,098612 | 1,008619 | 0,998532 | 98,02823 |
| ILMN_1229242 | F830016N17Rik | 992,1156 | 0,099309 | 985,5693 | 0,099541 |
| ILMN_2826304 | Fabp6 | 103,1885 | 1,00344 | 102,212 | 1,034919 |
| ILMN_3066293 | Fancc | 1006,906 | 0,990837 | 97,96588 | 1,010898 |
| ILMN_2847136 | Fastk | 99,51694 | 0,982594 | 100,8734 | 97,22678 |
| ILMN_1226274 | Fat4 | 99,91808 | 9,778576 | 102,6167 | 0,991788 |
| ILMN_3038394 | Fbxl10 | 1,000968 | 10,34846 | 1,003316 | 101,5194 |
| ILMN_2633301 | Fbxl7 | 0,996523 | 9,886947 | 1,002087 | 101,1812 |
| ILMN_2451855 | Fbxo45 | 0,097758 | 9,846192 | 0,977467 | 97,43176 |
| ILMN_2582084 | Fermt2 | 100,7731 | 0,997861 | 103,4975 | 1,018472 |
| ILMN_1229698 | Fgd4 | 0,968829 | 1,003967 | 0,994546 | 98,88624 |
| ILMN_2707356 | Fgf13 | 98,5557 | 0,979335 | 101,3539 | 0,989269 |
| ILMN_2832105 | Fgg | 976,712 | 1,022724 | 1000,745 | 0,982923 |
| ILMN_2748680 | Fhit | 1,027531 | 1,002197 | 0,992864 | 9753,363 |
| ILMN_2674132 | Fibp | 1,005565 | 1,001045 | 1,017715 | 99,94015 |
| ILMN_1260135 | Flnc | 0,970813 | 0,985748 | 0,101869 | 98,35351 |
| ILMN_2702464 | Flot1 | 100,5289 | 1,008288 | 98,87429 | 0,098905 |
| ILMN_2926842 | Flrt2 | 100,8743 | 0,99468 | 98,35319 | 0,95436 |
| ILMN_1248190 | Flvcr2 | 101,0148 | 0,866904 | 100,9189 | 0,886543 |
| ILMN_1240846 | Fndc1 | 100,1766 | 1,004825 | 104,85 | 0,099585 |
| ILMN_2670517 | Fntb | 1,004059 | 0,961594 | 0,983029 | 97,38121 |
| ILMN_1252110 | Foxj2 | 1,037745 | 0,09719 | 1,031479 | 93,83965 |
| ILMN_1224018 | Foxk1 | 0,955487 | 0,985807 | 0,995219 | 98,28413 |
| ILMN_2656498 | Foxo1 | 1,037234 | 1,00469 | 1,014846 | 100,0742 |
| ILMN_1251126 | Foxp3 | 9,77979 | 9,4417 | 9,726849 | 91,25276 |
| ILMN_2659663 | Foxp2 | 9,659801 | 1,0488 | 9,851438 | 1,012678 |
| ILMN_2429551 | Frmd4a | 0,102648 | 0,925808 | 1,019704 | 96,04416 |
| ILMN_2958016 | Fundc1 | 1,073253 | 1,094891 | 1,055057 | 109,6586 |
| ILMN_2674979 | Fus | 9,371913 | 1,012155 | 96,29235 | 1,005847 |
| ILMN_2939666 | Fzd2 | 992,6725 | 9,804943 | 1041,343 | 0,992843 |
| ILMN_2774825 | G3bp1 | 97,62113 | 1,012218 | 99,58618 | 1,000295 |
| ILMN_2646380 | Gabpb1 | 0,099944 | 1,112443 | 1,01149 | 1118,014 |
| ILMN_3106849 | Gal3st3 | 1,042885 | 100,5308 | 1,040509 | 99,52122 |
| ILMN_2881155 | Gal3st4 | 10,02421 | 0,998784 | 9,969722 | 99,38768 |
| ILMN_2860649 | Gbp6 | 100,0182 | 0,99548 | 95,27171 | 0,974757 |

TABLE 2-continued

| | | OVA-sa2,3 vs OVA 1 h | OVA-sa2,3 vs OVA 6 h | OVA-sa2,6 vs OVA 1 h | OVA-sa2,6 vs OVA 6 h |
|---|---|---|---|---|---|
| ILMN_2875336 | Gcat | 100,5076 | 0,958457 | 101,5154 | 9,983476 |
| ILMN_1228316 | Gdi1 | 0,102815 | 1,027637 | 1,006134 | 102,9727 |
| ILMN_1214319 | Gemin6 | 1,011646 | 0,992227 | 1,009633 | 97,57332 |
| ILMN_1236845 | Gfod2 | 0,09598 | 0,097142 | 0,98029 | 97,09654 |
| ILMN_2631363 | Gif | 0,983927 | 0,97706 | 0,965454 | 97,4734 |
| ILMN_2721734 | Gjd2 | 0,102873 | 1,01547 | 0,101304 | 966,5576 |
| ILMN_2685506 | Gje1 | 1,009132 | 0,990791 | 0,974513 | 1011,543 |
| ILMN_2838605 | Glis3 | 990,414 | 0,009946 | 990,063 | 0,996183 |
| ILMN_2729364 | Glra2 | 1,000599 | 0,994161 | 99,3303 | 9,891735 |
| ILMN_1217767 | Glrx5 | 0,094499 | 9,159094 | 0,955313 | 91,33761 |
| ILMN_1248467 | Gm1027 | 99,22358 | 0,100963 | 100,0698 | 0,102133 |
| ILMN_2539428 | Gm1070 | 0,959547 | 99,624 | 0,994394 | 1,012881 |
| ILMN_3029489 | Gm129 | 0,982231 | 1,020812 | 1,007998 | 96,58471 |
| ILMN_1232057 | Gm26 | 0,100459 | 0,099178 | 1,03716 | 101,3112 |
| ILMN_1240736 | Gm318 | 1,014537 | 0,986561 | 1,024794 | 9945,749 |
| ILMN_2598594 | Gm443 | 10,13529 | 0,994511 | 99,82462 | 0,980946 |
| ILMN_2803319 | Gm606 | 101,3642 | 0,099711 | 100,6399 | 1,037138 |
| ILMN_3022025 | Gm732 | 0,958279 | 9,656418 | 0,958082 | 98,94724 |
| ILMN_1229324 | Gm757 | 1,001783 | 1,018478 | 1,008558 | 102,8928 |
| ILMN_2908855 | Gnai2 | 9,832485 | 0,094289 | 9,895567 | 95,49658 |
| ILMN_2733433 | Gnai3 | 1020,027 | 0,103899 | 1028,753 | 0,987284 |
| ILMN_2661635 | Gyg | 104,6152 | 1,006181 | 106,0327 | 1,023016 |
| ILMN_2742160 | H13 | 96,85991 | 0,967374 | 100,4352 | 0,944166 |
| ILMN_2685581 | H2-Q5 | 1,010285 | 1,046776 | 10,058 | 106,6858 |
| ILMN_1230323 | Hbp1 | 9750,761 | 0,975145 | 9891,527 | 0,992563 |
| ILMN_2637982 | Herc1 | 0,991905 | 1,005105 | 0,009839 | 104,9426 |
| ILMN_2723631 | Hint1 | 99,59557 | 0,991124 | 98,94354 | 0,954837 |
| ILMN_1252995 | Hist1h2be | 9,861481 | 9,457645 | 9,881257 | 93,87584 |
| ILMN_2677408 | Hrmt1l2 | 0,967371 | 0,098508 | 0,975685 | 1013,349 |
| ILMN_2658501 | Ifitm3 | 1,029882 | 0,104393 | 1,038346 | 104,5469 |
| ILMN_2658633 | Ifna7 | 1,001601 | 10,32717 | 1,025378 | 100,0743 |
| ILMN_1260493 | Ift140 | 102,3462 | 0,999771 | 102,3426 | 0,096394 |
| ILMN_2671767 | Ift20 | 1,003421 | 1,043429 | 1,001482 | 102,5302 |
| ILMN_2788283 | Ift52 | 1,015203 | 9,422482 | 0,993875 | 92,56936 |
| ILMN_2590585 | Il1rapl2 | 9,950188 | 0,099529 | 9,807601 | 99,61221 |
| ILMN_3155812 | Il20rb | 0,099269 | 0,985523 | 0,999115 | 98,3642 |
| ILMN_1243066 | Il1a | 0,10371 | 0,164311 | 1,108696 | 0,016672 |
| ILMN_3155812 | Il20rb | 0,099269 | 0,985523 | 0,999115 | 98,3642 |
| ILMN_2590585 | Il1rapl2 | 9,950188 | 0,099529 | 9,807601 | 99,61221 |
| ILMN_2695883 | Irf6 | 98,07738 | 1,018216 | 99,05107 | 0,098528 |
| ILMN_2623699 | Irf4 | 10,11834 | 1,043845 | 10,07184 | 10,42105 |
| ILMN_2727022 | Itgb1bp3 | 0,099752 | 1,0138 | 10,24586 | 0,009991 |
| ILMN_2658633 | Ifna7 | 1,001601 | 10,32717 | 1,025378 | 100,0743 |
| ILMN_2711910 | Ifnb1 | 97,5166 | 1,045995 | 98,0811 | 1,078197 |
| ILMN_3046362 | Traf5 | 99,48784 | 1,130779 | 102,7819 | 1,093667 |
| ILMN_3087518 | Dido1 | 9,812321 | 1,018148 | 97,99077 | 1,019697 |
| ILMN_1228448 | Cd19 | 0,980663 | 0,009872 | 0,979249 | 9,960054 |
| ILMN_2977690 | Tm9sf4 | 0,992089 | 10,24256 | 0,980575 | 105,3711 |
| ILMN_2505970 | Tmc5 | 98,36548 | 0,986988 | 99,20843 | 0,958709 |
| ILMN_2732649 | Tmem107 | 99,31399 | 0,98021 | 101,2245 | 0,986103 |
| ILMN_2645662 | Tmem86a | 0,985481 | 8,866486 | 0,975585 | 878,4668 |
| ILMN_2441635 | Tomm34 | 101,2956 | 1,024865 | 1022,77 | 0,102703 |
| ILMN_1227012 | Ndufb4 | 0,985371 | 0,00103 | 0,09931 | 103,154 |
| ILMN_2419998 | Soat1 | 1,003797 | 8,423494 | 0,097272 | 83,96302 |
| ILMN_2607612 | Sp2 | 100,5908 | 1,00328 | 102,9451 | 0,103512 |
| ILMN_1221425 | Spaca5 | 0,973755 | 0,997833 | 9,798517 | 100,9814 |
| ILMN_1248179 | Spag11 | 98,6397 | 0,098584 | 96,21745 | 1,017883 |
| ILMN_1227250 | Specc1l | 0,963339 | 1,036285 | 0,930749 | 101,1408 |
| ILMN_1227250 | Specc1l | 0,963339 | 1,036285 | 0,930749 | 101,1408 |
| ILMN_2639777 | Sphk2 | 10,1154 | 1,011834 | 10,1043 | 100,6965 |
| ILMN_2818294 | Srpx2 | 100,8231 | 0,100387 | 98,63012 | 1,016853 |
| ILMN_3023573 | Ssbp1 | 100,3159 | 1,022076 | 98,92587 | 0,998213 |
| ILMN_2783117 | Tas2r140 | 98,39451 | 1,015511 | 97,5502 | 0,963632 |
| ILMN_2463080 | Tbx13 | 10,10685 | 10,24209 | 98,87766 | 101,2983 |
| ILMN_3072487 | Tcfap2b | 0,985614 | 9,853532 | 0,993813 | 1061,242 |
| ILMN_2650280 | Sod2 | 9,524808 | 1,131742 | 9,612056 | 0,115816 |
| ILMN_1227889 | Pias3 | 1,022192 | 1,025845 | 10,27761 | 1040,663 |
| ILMN_2631014 | Pias3 | 0,999235 | 1,004021 | 0,994658 | 98,45135 |
| ILMN_2770667 | Acin1 | 0,979681 | 0,097175 | 0,946506 | 99,56963 |
| ILMN_1216022 | Aclp7 | 1,00318 | 10,64468 | 10,17214 | 104,08 |

The invention claimed is:

1. A method for suppressing an immune response in a subject in need of such a treatment, the method comprising:

administering to the subject a N-acetylneuraminic acid (Neu5Ac) alpha modified antigen.

2. The method according to claim 1, wherein the subject has been diagnosed as suffering from an autoimmune disease.

3. The method according to claim 1, wherein the subject has been diagnosed as suffering from an inflammatory disease.

4. The method according to claim 1, wherein the sia alpha modified antigen is a Neu5Ac alpha 2,3 modified antigen or a Neu5Ac alpha 2,6 modified antigen.

* * * * *